United States Patent
Neumaier et al.

(10) Patent No.: US 11,542,234 B2
(45) Date of Patent: Jan. 3, 2023

(54) 2-ALKOXY-6-[18F]FLUORONICOTINOYL SUBSTITUTED LYS-C(O)-GLU DERIVATIVES AS EFFICIENT PROBES FOR IMAGING OF PSMA EXPRESSING TISSUES

(71) Applicant: Universität zu Köln, Cologne (DE)

(72) Inventors: Bernd Neumaier, Cologne (DE); Boris Zlatopolskiy, Cologne (DE); Philipp Krapf, Siegburg (DE); Raphael Richarz, Leverkusen (DE); Alexander Drzezga, Cologne (DE)

(73) Assignee: Universität zu Köln, Cologne (DE)

( * ) Notice: Subject to any disclaimer, the term of this patent is extended or adjusted under 35 U.S.C. 154(b) by 71 days.

(21) Appl. No.: 16/981,456

(22) PCT Filed: Mar. 15, 2019

(86) PCT No.: PCT/EP2019/056578
§ 371 (c)(1),
(2) Date: Sep. 16, 2020

(87) PCT Pub. No.: WO2019/175405
PCT Pub. Date: Sep. 19, 2019

(65) Prior Publication Data
US 2021/0032206 A1 Feb. 4, 2021

(30) Foreign Application Priority Data
Mar. 16, 2018 (EP) .................................... 18162380

(51) Int. Cl.
| | | |
|---|---|---|
| A61K 51/00 | (2006.01) | |
| A61M 36/14 | (2006.01) | |
| C07D 213/82 | (2006.01) | |
| A61K 51/04 | (2006.01) | |
| C07B 59/00 | (2006.01) | |

(52) U.S. Cl.
CPC ........ C07D 213/82 (2013.01); A61K 51/0455 (2013.01); C07B 59/002 (2013.01)

(58) Field of Classification Search
CPC .. C07D 213/82; A61K 51/0455; C07B 59/002
See application file for complete search history.

(56) References Cited

U.S. PATENT DOCUMENTS 10,112,974 B2  10/2018  Neumaier et al.
2017/0267717 A1  9/2017  Neumaier et al.

FOREIGN PATENT DOCUMENTS

WO  2016/030329 A1  3/2016
WO  WO-2017214470 A1 * 12/2017 ......... A61K 51/0497

OTHER PUBLICATIONS

Shen et al. J. Fluorine Chem. 128 (2007) 1461-1468.*
International Search Report dated Jun. 19, 2019 issued in corresponding PCT/EP2019/056578 application (4 pages).
V. Bouvet et al., "Automated Synthesis of [18F]DCFPyL Via Direct Radiofluorination and Validation in Preclinical Prostate Cancer Models", EJNMMI Research, vol. 6, No. 40 (2016) pp. 1-15.
Y. Chen et al., "2-(3-{1-Carboxy-5-[(6-[18F]Fluoro-Pyridine-3-Carbonyl)-Amino]-Pentyl}-Ureido)-Pentanedioic Acid, [18F]DCFPyL, a PSMA-Based PET Imaging Agent for Prostate Cancer", Clinical Cancer Research, vol. 17, No. 24 (2011) pp. 7645-7653.

* cited by examiner

*Primary Examiner* — Michael G. Hartley
*Assistant Examiner* — Sean R Donohue
(74) *Attorney, Agent, or Firm* — Millen White Zelano and Branigan, PC; Csaba Henter

(57) ABSTRACT

6-[$^{18}$F]Fluoro-2-alkoxynicotinoyl substituted Lys-C(O)-Glu derivatives were identified as efficient imaging probes for PSMA expressing tissues in comparison to other known PSMA specific ligands like [$^{18}$F]DCFPyL, [$^{68}$Ga]HBED-CC-PSMA, [$^{18}$F]PSMA-1007 and [Al$^{18}$F]HBED-CC-PSMA. Unexpectedly, the 6-[$^{18}$F]fluoro-2-alkoxy and 6-[$^{18}$F]fluoro-4-alkoxy substituted analogs showed significant differences in accumulation in PSMA expressing prostate tumor cells. Whereas the 2-alkoxy derivative showed cellular uptake values higher than [$^{18}$F]DCFPyL, the cellular uptake of the corresponding 4-alkoxy substituted derivative was significantly lower. Furthermore, in vivo PET studies with 2-alkoxy-substituted probes demonstrated excellent visualization of PSMA positive ganglia with extremely high target to background ratio. In contrast, the 4-alkoxy substituted derivatives showed less favorable biodistribution with significantly lower uptake in PSMA positive tissues. Especially, the $^{18}$F-labeled 2-methoxy derivate ((2S)-2-({[(1S)-1-carboxy-5-[(6-[$^{18}$F]fluoro-2-methoxypyridin-3-yl)formamido]pentyl]carbamoyl}-amino)pentanedioic acid) demonstrated exceptional clinical efficiency in detecting small PCa lesions, including those which could not be visualized with [$^{68}$Ga]HBED-CC-PSMA representing currently the gold standard for the diagnosis of recurrent PCa. Furthermore, this probe is easily accessible on a preparative scale in commercially available automated synthesis modules like GE FASTlab and TRACERlab FX N Pro. Consequently, the novel probe is a valuable tool for the visualization of ganglia and reendothelialization as well as for the diagnosis of glioma, neuropathic pain and atherosclerotic plaques.

19 Claims, 10 Drawing Sheets

2-ALKOXY-6-[18F]FLUORONICOTINOYL SUBSTITUTED LYS-C(O)-GLU DERIVATIVES AS EFFICIENT PROBES FOR IMAGING OF PSMA EXPRESSING TISSUES

BACKGROUND OF THE INVENTION

Prostate cancer (PCa) is the most commonly diagnosed cancer and the third leading cause of cancer-related death among men in Germany with 59,620 novel cases and 13,408 deaths in 2013.[1] 2-Deoxy-2-[$^{18}$F]fluoro-D-glucose ([$^{18}$F]FDG), which is an indicator of glycolytic activity in cancer cells, is generally ineffective in the diagnosis of localized PCa due to the low metabolic glucose activity of PCa compared with other cancer types.[2] Numerous studies revealed that PCa is associated with changes in fatty acid metabolism. Therefore, [$^{11}$C]choline, [$^{18}$F]fluoromethyl-, or [$^{18}$F]fluoroethylcholine, which target upregulated lipid synthesis, have been applied in molecular imaging of PCa.[3] However, normal and hyperplastic prostatic tissues may also accumulate choline-derived tracers, leading consequently to false positive diagnoses.[4]

PCa is characterized by an elevated level of glutamine metabolism.[5] Consequently, amino acid PET tracers were utilized for PCa imaging[6] Especially, anti-1-amino-3-[$^{18}$F]fluorocyclobutane-1-carboxylic acid ([$^{18}$F]FACBC), a conformationally restricted isoleucine analogue, demonstrated promising results in several clinical studies[7] and was approved by the FDA for the detection of recurrent PCa.[8] However, a meta-analysis of data of 251 patients showed a relatively high false positive rate for this probe in detecting recurrent PCa, with a sensitivity of 87% and a relatively low specificity of 66%.[9]

Prostate specific antigen (PSMA) expressed by the vast majority of prostate cancers is a particularly promising target for PCa imaging especially owing to the correlation of increased PSMA expression with tumor aggressiveness.[10] Consequently, PSMA imaging has great potential for the improvement of PCa diagnostics and staging. PCa is often initially diagnosed because of elevated levels of PSA in serum. However, diagnosis should be confirmed by biopsy.[11] Frequently, the first biopsy fails and needs to be repeated.[12] Furthermore, the choice of treatment, ranging from active surveillance to systemic therapy, should be made on the basis of the grade and stage of a tumor.[12] Consequently, the ideal procedure for PCa imaging should provide reliable data for disease staging.

At least in Europe, [$^{68}$Ga]Ga-PSMA-HBED-CC (FIG. 1) is already widely used for PCa diagnostics. However, the growing demand for easily accessible imaging agents for targeting PSMA stimulated the development of several $^{18}$F-labeled PET tracers.[13] Among them, [$^{18}$F]DCFPyL developed by Chen et al.[13c] plays an important role and was studied in several clinical centers.[14] Dietlein et al.[14a,15] reported the first comparisons between [$^{18}$F]DCFPyL and [$^{68}$Ga]HBED-CC-PSMA in patients with recurrent PCa. In these studies, [$^{18}$F]DCFPyL PET/CT imaging enabled the detection of additional lesions in 21 and 36% of the patients indicating a higher image quality in comparison to [$^{68}$Ga]Ga-PSMA-HBED-CC PET/CT.

Despite of the fact that [$^{18}$F]DCFPyL showed good imaging properties the tracer has some limitations with respect to the detection of very tiny lesions and pharmacokinetics. Thus, there is still an unmet need for the development of even more efficient $^{18}$F-labeled PSMA specific probes with very high target to background ratio.

It is the objective of the present invention to provide a description of an innovative PSMA selective PET tracer especially for imaging of prostate tumor. The objective of the present invention is solved by teaching of independent claims. Further advantageous features, aspects and details of the invention are evident from the dependent claims, the descriptions, the figures, and the examples of the presented application.

DESCRIPTION OF THE INVENTION

Subject matter of the present invention is a compound of the general formula (I):

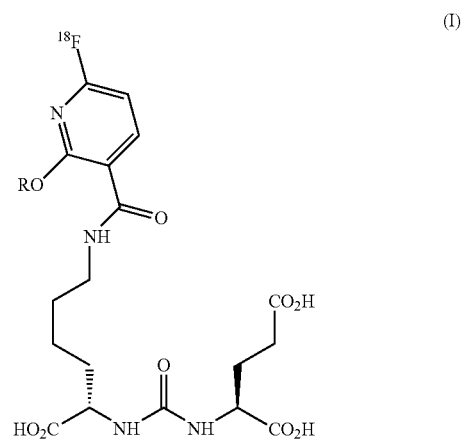

(I)

wherein R represents $C_1$-$C_{10}$ substituted or unsubstituted alkyl, $C_5$-$C_{12}$ unsubstituted or substituted aryl or heteroaryl.

In the context of the present invention, an alkyl group, if not stated otherwise, denotes a linear or branched $C_1$-$C_{10}$-alkyl, preferably a linear or branched chain of one to five carbon atoms; an alkenyl group, if not stated otherwise, denotes a linear or branched $C_2$-$C_{10}$-alkenyl; and an alkynyl group, if not stated otherwise, denotes a linear or branched $C_2$-$C_{10}$-alkynyl group, which may be substituted by one or more substituents R'.

Preferred alkyl maybe selected from $C_1$-$C_6$-alkyl, $C_3$-$C_6$-alkenyl and $C_3$-$C_6$-alkynyl.

The $C_1$-$C_6$-alkyl, $C_3$-$C_6$-alkenyl and $C_3$-$C_6$-alkynyl residue may be selected from the group consisting of —$CH_3$, —$C_2H_5$, —$C_3H_7$, —$CH(CH_3)_2$, —$CH_2$—CH═$CH_2$, —$CH_2$—C≡CH, —$C_4H_9$, —$CH_2$—CH($CH_3$)$_2$, —CH($CH_3$)—$C_2H_5$, —C($CH_3$)$_3$, —$C_5H_{11}$, —$C_6H_{13}$, —C(R')$_3$, —$C_2$(R')$_5$, —$CH_2$—C(R')$_3$, —$C_3$(R')$_7$, —$C_2H_4$—C(R')$_3$, —$C_2H_4$—CH═$CH_2$, —$CH_2$—CH═CH—$CH_3$, —$C_2H_4$—C≡CH, —$CH_2$—C≡C—$CH_3$, —$C_2H_4$—CH($CH_3$)$_2$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —$C_3H_6$—CH═$CH_2$, —$C_2H_4$—CH═CH—$CH_3$, —$CH_2$—CH═CH—$C_2H_5$, —$CH_2$—CH═CH—CH═$CH_2$, —$CH_2$—CH═C($CH_3$)$_2$, —$C_3H_6$—C≡CH, —$C_2H_4$—C≡C—$CH_3$, —$CH_2$—C≡C—$C_2H$, —$CH_2$—C≡C—CH═$CH_2$, —$CH_2$—CH═CH—C≡CH, —$CH_2$—C≡C—C≡CH, —$C_3H_6$—CH($CH_3$)$_2$, —$C_2H_4$—CH($CH_3$)—$C_2H_5$, —CH($CH_3$)—$C_4H_9$, —CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C(CH₃)₂—C₃H₇, —C(CH₃)₂—CH(CH₃)₂, —C₂H₄—C(CH₃)₃, —CH(CH₃)—C(CH₃)₃, —C₄H₅—CH=CH₂, —C₃H₆—CH=CH—CH₃, —CH₂—CH=CH—C₃H₇, —C₂H₄—CH=CH—C₂H₅, —CH₂—C(CH₃)=C(CH₃)₂, —C₂H₄—CH=C(CH₃)₂, —C₄H₅—C≡CH, —C₃H₆—C≡C—CH₃, —CH₂—C≡C—C₃H₇, and —C₂H₄—C≡C—C₂H₅;

An aryl group denotes an aromatic group having six to twelve carbon atoms, which may be substituted by one or more substituents R', and may be fused to another aromatic ring; the aryl group is preferably a phenyl group, -o-C6H4-R', -m-C6H4-R', -p-C6H4-R';

A heteroaryl group denotes a 4, 5- or 6-membered heterocyclic group which contains at least one heteroatom like O, N, S. This heterocyclic group can be fused to aromatic ring. For example, this group can be selected from a 3-tetrahydrofuranyl, 3-tetrahydrothienyl, thiazolidinyl, thiadiazolyl, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-oxadiazol-3-yl, 1,2,4-oxadiazol-5-yl, 1,2,5-oxadiazol-3-yl, benzoxazol-2-yl, benzoxazol-4-yl, benzoxazol-5-yl, benzoisoxazol-3-yl, benzoisoxazol-4-yl, benzoisoxazol-5-yl, 1,2,5-oxadiazol-4-yl, 1,3,4-oxadiazol-2-yl, 1,2,4-thiadiazol-3-yl, 1,2,4-thiadiazol-5-yl, 1,3,4-thiadiazol-2-yl, isothiazol-3-yl, isothiazol-4-yl, isothiazol-5-yl, benzoisothiazol-3-yl, benzoisothiazol-4-yl, benzoisothiazol-5-yl, 1,2,5-thiadiazol-3-yl, 1-imidazolyl, 2-imidazolyl, 1,2,5-thiadiazol-4-yl, 4-imidazolyl, benzoimidazol-4-yl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purinyl, phthalazinyl, pteridinyl, thiatetraazaindenyl, thiatriazaindenyl, isothiazolopyrazinyl, 6-pyrimidinyl, 2,4-dimethoxy-6-pyrimidinyl, benzimidazol-2-yl, 1H-benzimidazolyl, benzimidazol-4-yl, benz-imidazol-5-yl, benzimidazol-6-yl, benzimidazol-7-yl, tetrazolyl, tetrahydro-thieno[3,4-d]imidazol-2-one-yl, pyrazolo[5,1-c][1,2,4]triazinyl, isothiazolopyrimidinyl, pyrazolotriazinyl, pyrazolopyrimidinyl, imidazopyridazinyl, imidazopyrimidinyl, imidazopyridinyl, triazolotriazinyl, triazolopyridinyl, triazolopyrazinyl, triazolopyrimidinyl, or triazolopyridazinyl group. This heterocyclic group can be substituted by one or more substituents R', wherein R' is as defined above;

R' independently represents H, —C₂R'', —CONHR'', —CR''O, —CN, alkyl, alkoxy, —OH, halogen, haloalkyl or haloalkoxy;

A haloalkoxy group denotes an alkoxy group as defined above substituted by one or more halogen atoms, preferably substituted by one to five halogen atoms, the haloalkoxy group is preferably a —OC(R¹⁰)₃, —OCR¹⁰(R¹⁰')₂, —OCR¹⁰(R¹⁰')R¹⁰'', —OC₂(R¹⁰)₅, —OCH₂—C(R¹⁰)₃, —OCH₂—CR¹⁰(R¹⁰')₂, —OCH₂—CR¹⁰(R¹⁰')R¹⁰'', —OC₃(R¹⁰)₇ or —OC₂H₄—C(R¹⁰)₃, wherein R¹⁰, R¹⁰', R¹⁰'' represent F, Cl, Br or I, preferably F;

In one embodiment R represents C1-C4 substituted or unsubstituted alkyl. In another embodiment R represents C1-C3 substituted or unsubstituted alkyl. In another embodiment R represents methyl.

In one embodiment R represents

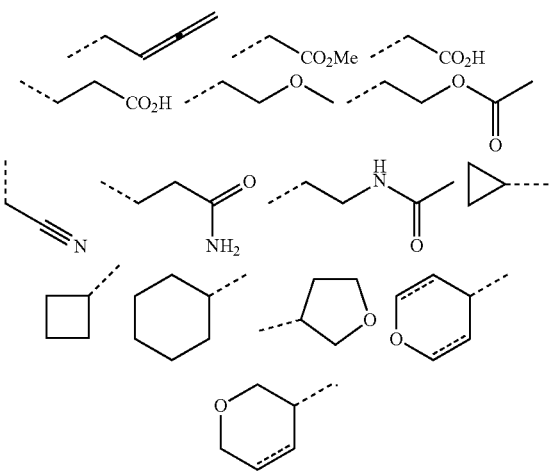

In one embodiment of the invention the compound of general formula (I) according to the present invention is for use in imaging of PSMA-positive organs or tissues or both in a subject.

PSMA-positive organs or tissues maybe the following: kidneys, salivary and lacrimal glands, healing wounds, clear-cell renal cell carcinoma, glioma, tumor-associated and not associated neovasculature, lung cancer, glioblastoma multiforme and breast carcinoma.

In one embodiment of the invention the compound of general formula (I) according to the present invention is for use in imaging of PSMA-positive organs or tissues or both in a subject wherein said subject has a pathological condition that is selected from the group comprising cancer, prostate cancer, reendothelialization, neuropathic pain and atherosclerosis.

In one embodiment of the invention the compound of general formula (I) according to the present invention is for use in staging a pathological or physiological condition associated with one or more PSMA-positive organs or tissues or both of a subject.

In one embodiment of the invention the compound of general formula (I) according to the present invention is for use in staging a pathological or physiological condition associated with one or more PSMA-positive organs or tissues or both of a subject wherein said subject has a pathological condition that is selected from the group comprising cancer, prostate cancer, reendothelialization, neuropathic pain and atherosclerosis. Neuropathic pain includes peripheral and central neuropathic pain. Cancer may be selected from the following: clear-cell renal cell carcinoma, glioma, tumor-associated neovasculature, lung cancer, glioblastoma multiforme and breast carcinoma.

On embodiment of the present invention is a method of making a compound of general formula (I) according to the present invention from precursors of a general formula II and Lys-C(O)-Glu comprising the steps of:

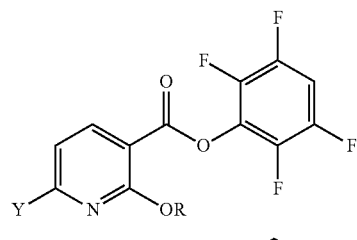

Y = Me$_3$N$^+$Z$^-$ or Z$^{-+}$N⟨⟩
Z$^-$ = CF$_3$SO$_3$ or CF$_3$CO$_2$
R = as above defined

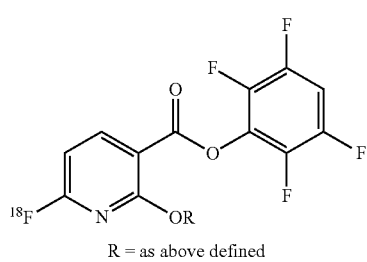

[$^{18}$F]III

R = as above defined

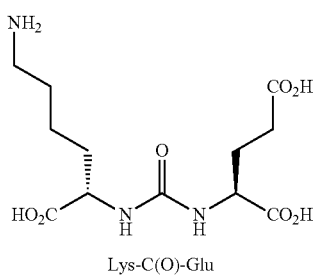

Lys-C(O)-Glu a) Providing an aqueous solution of [$^{18}$F]fluoride;
b) Loading of [$^{18}$F]fluoride onto a anion exchange resin;
c) Washing the anion exchange resin like QMA light (Waters), ChromaFix PS-HCO$_3$ (Machery-Nagel), Oasis WAC 3 cc (Waters), QMA carb (Waters) and Vac QMA 1 cc (Waters) or similar with a polar aprotic solvent like DMF, DMSO or MeCN, preferably MeCN or C$_1$-C$_6$ alcohol preferably MeOH or EtOH or with the mixture of thereof;
d) Drying the resin with the flow air or inert gas like He or Ar;
e) Elution of [$^{18}$F]fluoride with a solution of a precursor (II) in a polar aprotic solvent like DMF, DMSO or MeCN, preferably MeCN or a C$_2$-C$_6$ alcohol preferably EtOH or with the mixture of thereof, preferably MeCN/tBuOH;
f) If the elution was carried out using a C$_2$-C$_6$ alcohol diluting the reaction mixture with a polar aprotic solvent like DMF, DMSO or MeCN, preferably MeCN or aprotic solvent/C$_2$-C$_6$ alcohol mixture, preferably MeCN/tBuOH;
g) Heating of the resulting solution at 30-70° C. preferably at 40-50° C. for 1-30 min preferably for 2-7 min which furnishes the crude [$^{18}$F]III;
h) Purification of [$^{18}$F]III using reversed phase solid phase extraction (RP SPE) like Chromafix C18 (Machery-Nagel), Sep-Pak tC18 (Waters) or SepPak HLB (Waters), or similar as follows: dilution the above mixture with H$_2$O, loading the resulting solution on a RP SPE cartridge, washing the cartridge with H$_2$O, elution of the purified [$^{18}$F]II with C$_2$-C$_6$ alcohol, preferably EtOH;
i) Elution of [$^{18}$F]I directly to a solution of Lys-C(O)-Glu and base like CsHCO$_3$, RbHCO$_3$, tetraalkylammonium phosphate, bicarbonate or carbonate preferably tetraalkylammonium bicarbonate or carbonate most preferably Et$_4$NHCO$_3$ in anhydrous C$_2$-C$_6$ alcohol, preferably EtOH;
j) Heating the resulting solution at 30-70° C. preferably at 40-50° C. for 1-30 min preferably for 2-7 min;
k) Purification of the crude [$^{18}$F]I using RP SPE or alternatively RP HPLC;
l) Formulation.

In an alternative embodiment subject matter of the present invention is a method of making a compound of general formula (I) according to any of claims 1-4 from a precursor of general formula (IV) comprising the steps of:

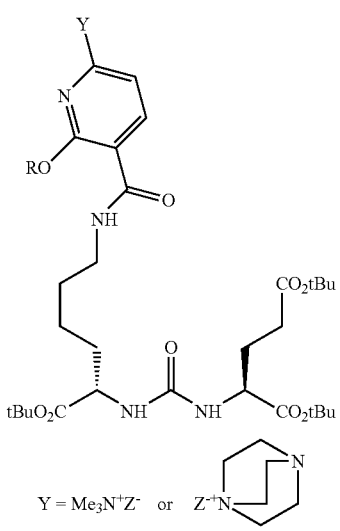

Y = Me$_3$N$^+$Z$^-$ or Z$^{-+}$N⟨⟩
Z$^-$ = CF$_3$SO$_3$ or CF$_3$CO$_2$
R = as above defined

[18F]V

R = as above defined a) Providing an aqueous solution of [8F]fluoride;
b) Loading of [18F]fluoride onto a anion exchange resin;
c) Washing the anion exchange resin like QMA light (Waters), ChromaFix PS-HCO$_3$ (Machery-Nagel), Oasis WAC 3 cc (Waters), QMA carb (Waters) and Vac QMA 1 cc (Waters) or similar with a polar aprotic solvent like DMF, DMSO or MeCN, preferably MeCN or C$_1$-C$_6$ alcohol preferably MeOH or EtOH or with the mixture of thereof;
d) Drying the resin with the flow air or inert gas like He or Ar;
e) Eluting of [18F]fluoride with a solution of a precursor (IV) in a C$_2$-C$_6$ alcohol preferably MeOH;
f) Evaporation of volatiles;
g) Dissolution of the residue in a polar aprotic solvent like DMF, DMSO, MeCN most preferably MeCN;
h) Heating of the resulting solution at 40-130° C. preferably 50° C. for 2-30 min preferably 5 min;
i) Addition of 85% H$_3$PO$_4$ or 10 M HCl to a solution of the crude [18F]V;
j) Heating of the resulting mixture at 40-130° C. preferably 50° C. for 2-30 min preferably for 5 min;
k) Dilution of the reaction mixture and adjustment of the pH to 2.0-2.5 with an aqueous solution of a base like NaHCO$_3$, Na$_2$CO$_3$, Et$_3$N, NaOH, Na$_2$HPO$_4$ and Na$_3$PO$_4$, preferably Na$_3$PO$_4$;
l) RP HPLC purification using H$_3$PO$_4$ in aqueous EtOH as an eluent;
m) Dilution with isotonic saline, adjustment of the pH with a base like NaHCO$_3$, Na$_2$CO$_3$, NaOH, Na$_2$HPO$_4$ and Na$_3$PO$_4$, preferably NaHCO$_3$ or Na$_2$HPO$_4$;
n) Sterile filtration.

In one embodiment of the present invention, the method does not comprise any evaporation steps; and/or wherein the method does not require any deprotection steps; and/or wherein the method does not require a neutralization step; and/or wherein the method does not require a formulation step.

One embodiment of the present invention is a kit or a cassette system for preparing a compound of the general formula (I) said kit or a cassette system comprises (i) an anion exchange column; (ii) a reaction vessel; (iii) vials containing aliquots of the appropriate eluents; (iv) a vial containing an aliquot of a precursor compound; (v) reagent vials wherein each reagent vial contains an aliquot of the appropriate reagent; (vi) optionally, one or more SPE columns for purification; (vii) optionally, HPLC column for purification and, (viii) means for cleaning said reaction vessel and said SPE columns.

An anion exchange column maybe selected from the group comprising QMA light (Waters), ChromaFix PS-HCO$_3$ (Machery-Nagel), Oasis WAC 3 cc (Waters), QMA carb (Waters), Vac QMA 1 cc (Waters) or similar.

Eluent(s) are preferably a polar aprotic solvent(s) selected from the group comprising a polar aprotic solvent like DMF, DMSO or MeCN, preferably MeCN or C$_1$-C$_6$ alcohol preferably MeOH or EtOH or with the mixture of thereof.

Precursor is a compound according to formula II or formula IV.

The reagent vials contain solvents like MeCN, DMF, DMSO, MeOH, EtOH, H$_2$O and saline, solutions of the salts like Et$_4$NHCO$_3$ or acids like HCl or H$_3$PO$_4$, solutions of precursors like II, IV or Lys-C(O)-Glu.

The reversed phase solid phase extraction (RP SPE) maybe selected from the group comprising Chromafix C18 (Machery-Nagel), Sep-Pak tC18 (Waters) or SepPak HLB (Waters) or similar.

Means for cleaning the reaction vessels maybe purging with acetone or EtOH and drying under a stream of He, Ar or air.

Subject matter of the present invention is a pharmaceutical composition comprising at least one compound of formula (I) together with at least one pharmaceutically acceptable solvent, ingredient and/or diluent.

Such solvent maybe diluted aqueous EtOH, DMSO, isotonic saline or phosphate buffered saline (PBS).

Such ingredient maybe PEG-400, ascorbinic or gentisic acid.

Such diluent maybe H$_2$O, isotonic saline or phosphate buffered saline (PBS).

Subject matter of the present invention is a pharmaceutical composition comprising at least one compound of formula (I) together with at least one pharmaceutically acceptable solvent, ingredient and/or diluent for use in imaging prostate cancer cells or prostate cancerous tissue.

EXAMPLES

Synthesis of Precursors for Radiolabeling

The corresponding onium triflate precursors of radiolabeled active esters, [18F]8 and [18F]9, were prepared by the reaction of 2,3,5,6-tetrafluorophenyl 6-chloro-2- or -4-methoxynicotinates (13 and 14, respectively) with Me$_3$N followed by anion metathesis using TMSOTf (FIG. 3). 13 and 14 were synthesized from the appropriate chloroanhydrides [obtained by the treatment of 6-chloro-2- or -4-methoxynicotinic acids (17 and 18, respectively) with oxalyl chloride in the presence of DMF traces] and 2,3,5,6-tetrafluorophenol using Et$_3$N as a base. 17 and 18 were prepared from 2,6- and 2,4-dichloronicotinic acids, respectively, by the reaction with MeONa, generated in situ from MeOH and NaH.[16] Similarly, the precursor of 2-EtO-6-[18F]FNic-OTfp (16) was prepared.

Example 01: Preparation of 2,3,5,6-tetrafluorophenyl-6-chloro-2-methoxynicotinate (6-Cl-2-OMe-Nic-OTfp, 13)

6-Chloro-2-methoxynicotinic acid (17) was prepared according to WO2012/110860 A1 or B. Drennen et al., *ChemMedChem* 2016, 11, 827-833. To a suspension of this compound (1.87 g, 9.97 mmol) in anhydrous CH$_2$Cl$_2$ (10 mL) was added oxalyl chloride (5 mL, 7.4 g, 58.3 mmol)

followed by DMF (1 drop, in 5 min an additional drop and in 10 min one more drop). After the vigorous gas evolution was ceased and the solid completely dissolved, the reaction mixture was concentrated using the argon flow and the residue was dried under reduced pressure affording the respective chloroanhydride (2.5 g, 100% crude) which was immediately used for the next step. To a solution of this compound in Et$_2$O (100 mL) was added 2,3,5,6-tetrafluorophenol (1.67 g, 10.06 mmol) followed by Et$_3$N (1.4 mL, 1.01 g, 10.9 mmol) and the resulting suspension was stirred for 16 h. Afterwards, the reaction mixture was washed with H$_2$O (3×20 mL), brine (2×20 mL), dried and concentrated under reduced pressure. The residue was recrystallized from hexane affording 13 (2.4 g, 72%) as a colorless solid.

$^1$H NMR (200 MHz, CDCl$_3$) δ ppm 4.12 (s, 3H) 7.02-7.12 (m, 2H) 8.38 (d, J=8.0 Hz, 1H)

$^{19}$F NMR (188.3 MHz, CDCl$_3$) δ ppm −138.9 (m), −152.5 (m)

$^{13}$C NMR (50.3 MHz, CDCl$_3$): δ ppm 55.2, 103.40 (t, J=27.9 Hz), 109.0, 116.7, 138.1 (m), 143.5 (m), 144.4, 148.6 (m), 154.6, 159.5, 163.0.

ESI HRMS: calcd for C$_3$H$_5$ClF$_4$NNaO$_3^+$: 356.97863; found: 356.97959.

Example 02: Preparation of 6-methoxy-N,N,N-trimethyl-5-(2,3,5,6-tetrafluorophenoxycarbo-nyl)pyridine-2-aminium triflate (6-NMe$_3^+$-OTf-2-OMe-Nic-OTfp, 7)

13 (1.53 g, 4.56 mmol) was dissolved in 2 M NMe$_3$ in THF (10 mL; stored over CaH$_2$) and the resulting solution was stirred for 3 h. A colorless solid began to precipitate within first 5 min. After 3 h all volatiles were removed at ≤30° C. using the argon flow and the residue was taken up in anhydrous Et$_2$O (30 mL) which was removed using the argon flow. The residual solid was carefully washed with anhydrous Et$_2$O and dried under reduced pressure affording the corresponding chloride salt (1.80 g, 100% crude) as a colorless solid which was immediately used for the next step.

TMSOTf (2.5 mL, 3.04 g, 13.68 mmol) was added to a suspension of the prepared chloride salt (1.8 g, max. 4.56 mmol) in anhydrous CH$_2$Cl$_2$ (10 mL) and the mixture was stirred for 30 min. The resulting clear solution was concentrated under reduced pressure and the residue was triturated with Et$_2$O and recrystallized from EtOAc affording 6 (1.81 g, 78% over two steps) as a colorless solid. The mother liquor was concentrated under reduced pressure and recrystallized from EtOAc giving the second crop of 6 (0.3 g, overall 92%).

$^1$H NMR (200 MHz, DMSO-d$_6$) δ ppm 2.88 (s, 9H) 3.38 (s, 3H) 6.70 (tt, J=10.5, 7.3 Hz 1H) 6.90 (d, J=8.2 Hz, 1H) 8.01 (d, J=8.2 Hz, 1H).

$^{19}$F NMR (188.3 MHz, DMSO-d$_6$) δ ppm −155.5 (m), −141.1 (m), −80.05 (m).

$^{13}$C NMR (50.3 MHz, DMSO-d$_6$) δ ppm 46.2, 46.7, 95.30, 95.8 (t, J=23.4 Hz), 98.5, 105.1, 109.1, 115.5, 130.1 (m), 135.6 (m), 138.9, 140.6 (m), 149.7 (q, J=45.3 Hz), 154.3.

ESI HRMS: calcd for C$_{16}$H$_{15}$O$_3$N$_2$F$_4$: 359.10133; found: 359.10124.

Example 03: Preparation of 2,3,5,6-tetrafluorophenyl-6-chloro-4-methoxynicotinate (6-Cl-4-OMe-Nic-OTfp. 14)

6-Chloro-4-methoxynicotinic acid (18) was prepared according to Ehara et al., *ACS Med Chem. Len.* 2014, S, 787-792. To a suspension of this compound (3.87 g, 9.97 mmol) in oxalyl chloride (25 mL, 37 g, 291.5 mmol) was added DMF (0.8 mL) followed by anhydrous CH$_2$Cl$_2$ (10 mL) and the reaction mixture was stirred 2 h at 60° C. Afterwards the reaction mixture was concentrated using the argon flow and the residue was dried under reduced pressure affording the respective chloroanhydride (4.0 g, 100% crude) which was immediately used for the next step. To a solution of this compound in hot EtOAc (100 mL) was added 2,3,5,6-tetrafluorophenol (2.92 g, 19.35 mmol; vigorous gas evolution was observed). Thereafter, the mixture was cooled to ambient temperature, Et$_3$N (2.68 mL, 1.96 g, 19.35 mmol) was added dropwise and the resulting suspension was stirred for 1 h. Afterwards, the reaction mixture was washed with H$_2$O (3×20 mL), brine (2×20 mL), dried and concentrated under reduced pressure. The residue was taken up in CH$_2$Cl$_2$ (70 mL), the suspension was filtered, the filter cake was washed with CH$_2$Cl$_2$ (50 mL). The collected dichloromethane fraction was concentrated under reduced pressure. The residue was recrystallized from hexane affording 14 (2.6 g, 44%) as a colorless solid. The mother liquor was concentrated by reduced pressure and the residue was purified by column chromatography (CH$_2$Cl$_2$:hexane=8:2.5) giving the second crop of 14 (0.8 g, total 58%).

$^1$H NMR (200 MHz, CDCl$_3$) δ ppm 4.04 (s, 3H) 6.89-7.18 (m, 2H) 8.98 (s, 1H)

$^1$H NMR (400 MHz, DMSO-d$_6$) δ ppm 4.04 (s, 3H) 7.53 (s, 1H) 8.00 (tt, J=10.93, 7.42 Hz, 1H) 8.90 (s, 1H).

$^{19}$F NMR (188.3 MHz, CDCl$_3$) δ ppm −152.4 (m), −138.7 (m).

$^{13}$C NMR (100.56 MHz, DMSO-d$_6$) δ ppm 57.5, 104.5, 104.8 (t, J=23.6 Hz), 109.2, 112.0, 128.3 (m), 138.9 (m), 141.3 (m), 144.3 (m), 146.8 (m), 152.9, 157.1, 159.1, 167.1.

ESI HRMS: calcd for C$_{13}$H$_7$CF$_4$NO$_3^+$: 336.00451; found: 336.00541.

Example 04: Preparation of 4-methoxy-N,N,N-trimethyl-5-(2,3,5,6-tetrafluorophenoxycarbo-nyl)pyridine-2-aminium triflate (6-NMe$_3^+$-OTf-4-OMe-Nic-OTfp, 7)

The title compound (1.09 g, 79%; colorless solid) was prepared from 14 (1.07 g, 2.71 mmol) using 2 M NMe$_3$ in THF (10 mL; stored over CaH$_2$) and TMSOTf (1.44 mL, 1.77 g, 17.96 mmol) as described in Example 02 for 13.

$^1$H NMR (400 MHz, DMSO-d$_6$) δ ppm 3.65 (s, 9H) 4.17 (s, 3H) 7.89 (s, 1H) 7.96-8.13 (m, 1H) 9.11 (s, 1H)

$^{19}$F NMR (188.3 MHz, DMSO-d$_6$) δ ppm −153.0 (m), −138.8 (m), −77.7 (m).

$^{13}$C NMR (100.56 MHz, DMSO-d$_6$) δ ppm 54.7, 58.1, 101.4, 105.0 (t, J=23.6 Hz), 114.3, 120.6 (q, J=241.6 Hz), 128.2 (m), 138.7 (m), 141.2 (m), 144.4 (m), 146.8 (m), 151.6, 158.7, 161.9, 168.51.

ESI HRMS: calcd for C$_{16}$H$_{15}$O$_3$N$_2$F$_4^+$: 359.10133; found: 359.10262.

Example 05: Preparation of 1,5-di-tert-butyl (2S)-2-({[(2S)-1-(tert-butoxy)-6-[(6-fluoro-2-methoxypyridin-3-yl)formamido]-1-oxohexan-2-yl] carbamoyl}amino)pentanedioate (6-F-2-OMe-Nic-Lys(OtBu)-ureido-Glu(OtBu)$_2$. 20)

A solution of 6 (0.71 g, 1.4 mmol) and H-Lys-OtBu-ureido-Glu(OtBu)$_2$ (0.53 g, 1.09 mmol, prepared according to Mirelli et al., *J. Am. Soc.* 2009, 131, 17090-17092) in anhydrous CH$_2$Cl$_2$ (5 mL) was incubated by ambient temperature for 72 h. The mixture was concentrated under reduced pressure and the residue was purified by column chromatography (first MeCN and, thereafter, $CH_2Cl_2$:MeOH=6:1) affording 5-{[(5S)-5-({[(2S)-1,5-bis(tert-butoxy)-1,5-dioxopentan-2-yl]carbamoyl}amino)-6-(tert-butoxy)-6-oxohexyl]carbamoyl}-6-methoxy-N,N,N-trimethyl-pyridine-2-aminium triflate (0.65 g, 72%) as a colorless foam, which was directly used for the next step.

Hexafluorobenzene (82 μL, 132 mg, 0.71 mmol) was added dropwise to a solution of $Bu_4NCN$ (1.15 g, 4.26 mmol) in anhydrous MeCN (4.3 mL), the resulting dark-red solution was stirred to the above triflate (0.59 g, 0.71 mmol) and the mixture was stirred for 16 h and taken up with $Et_2O$ and $H_2O$ (50 mL of each). The ethereal layer was separated and washed with $H_2O$ (3×20 mL), brine (2×20 mL), dried and concentrated under reduced pressure. The residue was purified by column chromatography ($Et_2O$) and sonication with pentane to give 20 (0.31 g, 68%) as a viscous yellow oil. $R_f$=0.36 (EtOAc:hexane=1:1).

$^1H$ NMR (300 MHz, $CDCl_3$) δ ppm 1.10-1.31 (m, 1H) 1.42 (s, 9H) 1.44 (s, 9H) 1.44 (s, 9H) 1.46-1.52 (m, 1H) 1.55-1.73 (m, 3H) 1.75-1.93 (m, 2H) 1.97-2.17 (m, 1H) 2.18-2.45 (m, 2H) 3.43 (d, J=6.3, 19.6 Hz, 2H) 4.08 (s, 3H) 4.20-4.45 (m, 2H), 4.79-5.78 (br, 2H) 6.62 (dd, J=8.2, 3.1 Hz, 1H) 7.76 (t, J=5.50 Hz, 1H) 8.63 (t, J=8.2 Hz, 1H).

$^9F$ NMR (282 MHz, $CDCl_3$) δ ppm −65.45 (dd, J=8.2, 2.7 Hz).

$^{13}C$ NMR (75.5 MHz, $CDCl_3$): δ ppm 22.5, 27.95, 27.97, 28.03, 28.5, 29.1, 31.5, 32.3, 39.3, 52.9, 53.4, 54.9, 80.5, 81.6, 81.9, 101.7 (d, J=35.5 Hz), 113.2 (d, J=5.3 Hz), 146.9 (t, J=9.1 Hz), 156.9, 159.9 (d, J=14.3 Hz), 162.8 (d, J=246.9 Hz), 163.0, 172.0, 172.3, 172.4.

Example 06: Preparation of (2S)-2-({[(1S)-1-carboxy-5-[(6-fluoro-2-methoxypyridin-3-yl)formamido]pentyl]carbamoyl}amino)pentanedioic acid (1)

A solution of 20 (0.31 g, 0.66 mmol) in $TFA/TIS/H_2O$=95/2.5/2.5 (10 mL) was incubated for 90 min at ambient temperature. Afterwards, all volatiles were removed under reduced pressure and the residue was taken up in TFA (10 mL), the resulting solution was incubated at ambient temperature for 3 h and concentrated under reduced pressure. The residue was sonicated with $Et_2O$ and recrystallized from $MeOH/Et_2O$ affording 1 (80 mg, 36%) as a colorless solid. The mother liquor was concentrated under reduced pressure and the residue was recrystallized from $MeOH/Et_2O$ to give the second crop of the title compound (45 mg, overall 56%).

$^1H$ NMR (300 MHz, $CD_3OD$) δ ppm 1.43-1.57 (m, 2H) 1.58-1.80 (m, 3H) 1.81-1.98 (m, 2H) 2.07-2.22 (m, 1H) 2.32-2.49 (m, 2H) 3.41 (t, J=6.87 Hz, 2H) 4.06 (s, 3H) 4.22-4.37 (m, 2H) 6.70 (dd, J=8.15, 2.89 Hz, 1H) 8.39 (t, J=8.15 Hz, 1H).

$^{19}F$ NMR (282 MHz, $CD_3OD$) δ ppm −67.67 (dd, J=7.80, 3.04 Hz).

$^{13}C$ NMR (75.5 MHz, $CD_3OD$): δ (ppm) 24.2, 29.1, 30.2, 31.2, 33.3, 40.8, 53.7, 54.2, 55.5, 102.3 (d, J=36.2 Hz), 115.2 (d, J=5.3 Hz), 147.1 (d, J=9.1 Hz), 160.3, 161.9 (d, J=14.3 Hz), 162.94 165.71 (d, J=209.1 Hz), 166.2, 175.9, 176.5, 176.6.

ESI HRMS: calcd for $C_{19}H_{25}O_9N_4FK^+$: 511.12372; found: 511.12366; calcd for $C_{19}H_{25}O_9N_4FNa^+$: 495.14978; found: 495.14959; calcd for $C_{19}H_{26}O_9N_4F^+$: 473.16784; found: 473.16756.

Radiosynthesis of [$^{18}F$]1 and [$^{18}F$]2

The novel PET tracers, [$^{18}F$]1 and [$^{18}F$]2, and [$^{18}F$]DCFPyL ([$^{18}F$]4) were prepared by the acylation of Lys-CO-Glu urea 10 with the appropriate $^{18}F$-labeled active ester, [$^{18}F$]8 and [$^{18}F$]9, in EtOH using $Et_4NHCO_3$ as a base (FIG. 2).[17] The corresponding radiofluorinated active esters were prepared by the elution of the [$^{18}F$]fluoride loaded on a anion exchange resin with a solution of the radiolabeling precursor in a suitable solvent (EtOH, EtOH/MeCN/tBuOH, MeCN/tBuOH or MeCN) followed by heating of the resulting solution to 40° C. for 2-5 min (if pure EtOH was used as an eluent, it was preliminary diluted with MeCN/tBuOH mixture). The crude radiolabeled active esters were purified by solid phase extraction Alternatively, [$^{18}F$]1 and [$^{18}F$]2 could be prepared using the one-pot two-step procedure similar to that proposed for the preparation of [$^{18}F$]DCFPyL by Bouvet et al.[18] and Ravert et al.[19] [$^{68}Ga$]Ga-PSMA-HBED-CC was synthesized according to Eder et al.,[20] [$^{18}F$]AlF-PSMA-HBED-CC and PSMA-1007 were produced according to Boschi et al.[21] and Cardinale et al.[22], respectively.

Example 07: Manual Synthesis of [$^{18}F$]1

Aqueous [$^{18}F$]fluoride (0.05-50 GBq) was loaded onto a Sep-Pak Accell Plus QMA carbonate plus light cartridge (Waters GmbH, Eschborn, Germany) preconditioned with 1 mL EtOH followed by 10 mL $H_2O$. The resin was washed with anhydrous EtOH (3 mL) and [$^{18}F$]fluoride was eluted into the reaction vessel with a solution 6 (10 mg, 21 μmol), in anhydrous EtOH (200 μL). The resin was then washed with anhydrous MeCN/tBuOH 1:4 (2 mL) into the reaction vessel too. The mixture was allowed to stir at 45° C. for 15-20 min. After that, the crude mixture was diluted with water (10 mL) and the solution was loaded onto a polymer RP or C-18 cartridge. The cartridge was washed with water (10 mL) and [$^{18}F$]8 was eluted with EtOH (500 μL). Alternatively, the anion exchange resin was washed with anhydrous MeCN (3 mL) and [$^{18}F$]fluoride was eluted into the reaction vessel with a solution 6 (12 mg, 25 μmol), in anhydrous MeCN/tBuOH 1:4 (0.6 mL). The resin was then flushed with anhydrous MeCN/tBuOH 1:4 (1 mL) into the reaction vessel, too. The mixture was allowed to stir at 40° C. for 1-3 min, diluted with water (10 mL) and the solution was loaded onto a polymer RP or C-18 cartridge. The cartridge was washed with water (10 mL) and [$^{18}F$]8 was eluted with EtOH (500 μL) directly to a solution of Lys-C(O)-Glu (2.5 mg, 7.8 μmol) in 0.19 M $Et_4NHCO_3$ in anhydrous EtOH (160 μL) and the reaction mixture was allowed to stir for 3-5 min at 45° C. The mixture was quenched with 0.1% TFA (20 mL) and loaded onto a preconditioned Sep-Pak C18 plus long cartridge. The cartridge was washed with water (10 mL) and after that plugged to a Sep Pak HLB short cartridge. [$^{18}F$]1 was transferred from the C18 onto the HLB resin by 1.7% $H_3PO_4$ in 6% EtOH (60 mL). HLB cartridge was washed with water (10 mL) and the product [$^{18}F$]PSMA-7 eluted with 50% EtOH in isotonic saline (2 mL). (FIG. 7)

Example 08: Automated Production of [$^{18}F$]1 on FXNPro Module (GE) Starting from [$^{18}F$]Fluoride without HPLC Purification Aqueous [$^{18}F$]fluoride (0.05-50 GBq) was transferred from the cyclotron target into a trapping vial and thereafter loaded onto a anion-exchange resin cartridge (Sep-Pak QMA carbonate light 46 mg, preconditioned with 1 mL water) from the male side of the cartridge. [$^{18}O$]$H_2O$ was collected in a separate vial. The cartridge was subsequently washed with MeCN (4 mL) from vial V1 from the female side of the cartridge. Washings were discarded. Thereafter, [$^{18}$F]fluoride was slowly eluted from the resin with a solution of 6 (10 mg, 20 µmol) in tBuOH:MeCN (4:1) (1 mL) from the vial V2 into reactor R1 using a stream of He. Afterwards, MeCN (2 mL) from vessel V3 was passed through the cartridge into reactor R1. Reactor R1 was filled with He, sealed and the reaction mixture was heated at 45° C. for 3 min. After cooling to ambient temperature the reaction mixture was diluted with $H_2O$ (15 mL) from vessel V5 and loaded onto a polymer RP cartridge (Strata X, preconditioned with 1 mL EtOH followed by 5 mL $H_2O$). The cartridge was washed with $H_2O$ (10 mL) from vial V4D and dried using a flow of helium for 5 min.

[$^{18}$F]8 was eluted with a freshly prepared solution of Lys-C(O)-Glu (4.6 mg, 15.2 µmol) and $Et_4NHCO_3$ (11.6 mg, 60.6 µmol) in EtOH (1 mL) from vial VX4 into reactor R2. The reaction mixture was heated at 40° C. for 3 min. After cooling to ambient temperature the reaction mixture was diluted with water (1 mL) from vial V7 and transferred to vessel CV3 containing 0.1% TFA (20 mL). The acidic solution was loaded onto a tC18 cartridge (Sep-Pak tC18 Plus Long Cartridge, 900 mg, preconditioned with 10 mL EtOH followed by 30 mL '$H_2O$). The cartridge was subsequently washed with water (10 mL) from vial V35 and [$^{18}$F]1 was eluted with 1.7% $H_3PO_4$ in 12% EtOH (60 mL) onto a HLB catridge (Oasis HLB Plus Short Cartridge 225 mg, preconditioned with 10 mL EtOH followed by 30 mL $H_2O$) from vessel V9. The HLB cartridge was washed with 10 mL water from vessel V43 and the purified [$^{18}$F]1 was eluted with 50% EtOH in isotonic saline (2 mL). The resulting solution was diluted with isotonic saline (9 mL) and sterile filtered. Quality control: eluent: 1.7% $H_3PO_4$ 10% EtOH for 5 min, then 50% EtOH for 2 min. Flow rate: 3 mL/min. Column: Chromolith® SpeedROD RP-18e column (Merck, Darmstadt Germany), 50×4.6 mm. Retention times: [$^{18}$F]1=3 min; [$^{18}$F]6=5.7 min.

Example 09: Automated Synthesis of [$^{18}$F]1 on GE FASTlab

Assembling of the Cassette

The cassette for the production of [$^{18}$F]1 (FIG. 8) was assembled using original components available from GE. First, the spike at B was connected by short flexible silicone tubing with the female side of a QMA carbonate light cartridge installed at C. At position A a short flexible silicone tubing was mounted for connection with the [$^{18}$O]$H_2O$ collection bottle. At positions D, O and U long flexible silicone tubings were installed to connect the cassette with large solvent storage bottles. A polymer reactor was connected using short silicone tubing to positions F, G and by long tubing to position V (the middle riser of the reactor was connected to valve G). At position H a small Cis cartridge was installed (Chromafix C18 ec, 250 mg) with the female side connected by long silicone tubing to R. At I, a 10 mL disposable vial with isotonic saline was installed using short silicone tubing. In slots J, K, L, and N small reagent vials were installed. Two types of reagent vials were used: 3 mL glass vial with 11 mm neck (260 µL dead volume), and a 5 mL glass vial with 13 mm neck (250 µL dead volume). The vials were closed with a rubber stoppers and crimped with aluminum caps.

During filling of the vial with the appropriate reagents, the dead volume had to be taken into account. For example, the 3 mL vial containing [$^{18}$F]6 precursor had to be filled with 23 mg precursor instead of the actually needed 10 mg.

However, filling of the vial with 460 µL EtOH would be equal to a solution of 10 mg precursor/200 µL (as it is required for the synthesis) plus a non-recoverable fraction of 260 µL. Vial J was a 3 mL type, containing 460 µL EtOH and 23 mg precursor 6. Vial K was a 5 mL type, containing 2.25 mL tBuOH/MeCN 4:1. Vial L was a 5 mL type and contained a solution of Lys-C(O)-Glu (2.5 mg, 7.8 µmol) and $Et_4NHCO_3$ (5.7 mg, 30 µmol) in anhydrous EtOH (750 µL). Vial N was a 5 mL type and contained 4.5 mL of 0.5% aqueous TFA. Slot M was equipped with a special spike used for the connection to a sterilized water bottle. At position P a Sep Pak C18 plus long cartridge was mounted with the female side connected by short silicone tubing to Q. At position T an Oasis HLB Plus Short Cartridge was mounted with the female side connected by a short silicone tubing to position S.

Radiosynthesis (cf FIG. 9)

The synthesizer was reseted and the self-check was performed by default. After passing the preliminary tests, the cassette was mounted and a programmed cassette self-test was performed to confirm leak-tightness of the cassette components. After passing this test, the tubing at D (EtOH), I (saline) and O (phosphoric acid) were connected. A 250 mL sterilized water bottle was connected via the spike at position M. Lines A and U were connected to the [$^{18}$O]$H_2O$ collection vessel and product vial, respectively. Afterwards, a programmed procedure was started to activate the SPE cartridges: the QMA carbonate light cartridge at C was preconditioned with $H_2O$ (1 mL). The Chromafix C18 RP cartridge at H was preconditioned with EtOH (1 mL) followed by $H_2O$ (3 mL). The Sep-Pak C18 Plus Long Cartridge at P and Oasis HLB Plus Short Cartridge at T were preconditioned with EtOH (3 mL) followed by $H_2O$ (20 mL). All reagent vials except the storage bottles at D, I, O were pressurized with helium (+1000 mbar). After these preliminary steps, the cassette was ready to start the synthesis.

Irradiated $^{18}$O-water (1.5 mL) was transferred from the cyclotron target to the receiver vial at position E and loaded onto the QMA carbonate light cartridge at C. The cartridge was subsequently washed with EtOH (2×1 mL from storage vessel D) by activation of S1. Thereafter, [$^{18}$F]fluoride was eluted stepwise into the reactor from the resin with a solution of 6 in EtOH (200 µL) stored in vial J. MeCN/tBuOH 1:4 (2 mL) from vial K was passed through the QMA cartridge into the reactor. Afterwards, lines were flushed with helium into the reactor to recover any residual activity. Thereafter, the reactor was sealed and heated at 50° C. for 15 min.

The reactor was charged by a constant low flow of helium to ensure pressure equalization, and the reaction mixture was quenched with $H_2O$ (2 mL) from reservoir M by activation of syringe 2 (S2). Syringe 2 was filled with $H_2O$ (4 mL), an aliquot of crude [$^{18}$F]8 (500 µL) and air (500 µL) to ensure proper mixing. The solution was loaded onto the C18 resin at position H. This stepwise dilution procedure was performed at least four times until full recovery of the reaction mixture in the reactor has been achieved. The C18 cartridge was washed with $H_2O$ (10 mL) and dried with a stream of helium (15 s). Afterwards, the reactor, the manifold, tubing H→R and yringe 1 were thoroughly cleaned with EtOH. Consequently, purified [$^{18}$F]8 was eluted into the reactor from the C18 resin with a solution of Lys-C(O)-Glu and to $Et_4NHCO_3$ in EtOH from the storage vessel at position L. Then, the reactor was sealed and heated at 40° C. for 3 min and supplied with a constant low flow of helium to ensure pressure equalization. Subsequently, the reaction mixture was quenched with 0.5% TFA (4 mL). The acidic solution of crude [$^{18}$F]1 was loaded onto the Sep-Pak tC18 Plus Long cartridge at position P. The cartridge was washed with H$_2$O (2×5 mL) and dried by applying a high flow of nitrogen (15 s). The C18 cartridge was switched in line with the SepPak HLB plus short at position T and 1.7% H$_3$PO$_4$ in 12% EtOH (60 mL) from the storage vessel connected by tubing at O was passed through both cartridges, and [$^{18}$F]1 was trapped onto the HLB resin. The HLB cartridge was washed with H$_2$O (10 mL) and purified [$^{18}$F]1 was eluted with ethanol (500 µL) from reservoir D into storage syringe 3 (S3). An ethanolic solution of [$^{18}$F]1 in syringe 3 was diluted with isotonic saline (10 mL) from vessel I. The resulting radiotracer solution was dispensed upon request into a vial at position U.

Example 10 Biological Evaluation of [$^{18}$F]1 and [$^{18}$F]2 in Comparison to Known PSMA Specific Tracers Within our ongoing program on the development of the novel PSMA-specific PET ligands we prepared and evaluated 6-[$^{18}$F]fluoro-2- and 4-methoxynicotinoyl substituted probes (2- and 4-MeO-[$^{18}$F]PSMA, [$^{18}$F]1 and [$^{18}$F]2, respectively) (FIG. 1). The biological properties of the novel compounds were compared with those of the known PSMA-specific PET tracers such as [$^{68}$Ga]Ga-PSMA-HBED-CC, [$^{18}$F]DCFPyL, [$^{18}$F]AlF-PSMA-HBED-CC[21] and [$^{18}$F]PSMA-1007.[23]

Cellular Uptake Experiments

The cellular uptake of the novel PET probes in PSMA positive LNCaP C4-2 and PSMA negative PC3 prostate tumor cell line in the presence and absence of 2-(phosphonomethyl)pentanedioic acid (2-PMPA; 20), known nanomolar PSMA inhibitor,[24] was measured and compared with that of [$^{18}$F]DCFPyL carried out in parallel (FIG. 4A). 2-MeO-[$^{18}$F]PSMA demonstrated a much higher uptake in PSMA$^+$ LNCaP C4-2 cells than [$^{18}$F]DCFPyL after 2 h incubation (2.03±0.03 vs. 1.55±0.05% ID/10$^5$ cells). The difference in the accumulation of the both tracers in the same cells after 4 h incubation was less pronounced (3.31±0.01 and 3.1±0.03% ID/10$^5$ cells for 2-MeO-[$^{18}$F]PSMA and [$^{18}$F]DCFPyL, respectively). The PSMA specificity of the tracer uptake in LNCaP C4-2 was confirmed by complete inhibition with 2-PMPA (≤0.1% ID/10$^5$ cells). The enrichment of both tracers in PSMA$^-$ PC3 cells was negligible (≤0.1% ID/10$^5$ cells). In contrast, the cellular uptake of 4-MeO-[$^{18}$F]PSMA in LNCaP C4-2 cells was significantly lower than that of [$^{18}$F]DCFPyL (0.79±0.04 vs. 1.53±0.03% ID/10$^5$ cells (after 2 h incubation) and 0.90±0.04 vs. 3.16±0.01% ID/10$^5$ cells (after 4 h incubation) (FIG. 4B). As in the case of 2-MeO-[$^{18}$F]PSMA the intracellular accumulation of 4-MeO-[$^{18}$F]PSMA in LNCaP C4-2 cells was completely blocked by 2-PMPA and was very low in PSMA negative PC3 cells.

Example 11: Cellular Uptake of [$^{18}$F]1 and [$^{18}$F]2 in PSMA$^-$ PC-3 Cells and PSMA$^+$ LNCaP C4-2 Cells Cell culture: PC3 and LNCaP C4-2 prostate tumor cells were generous gifts of G. Winter (Ulm, Germany).

PSMA$^-$ PC-3 cells were cultured in RPMI-1640 medium supplemented with FBS (10%) and penicillin/streptomycin (1%). PSMA* LNCaP C4-2 cells were cultured in a mixture of DMEM: Ham's F-12K (Kaighn's) mediums (4:1) supplemented with FBS (5%), NaHCO$_3$ (3 g/L), insulin (5 µg/mL), triiodothyronine (13.6 µg/mL), transferrin (5 µg/mL), biotin (0.25 µg/ml) and adenine (25 µg/mL). Both cell lines were grown in 75 mL flasks containing 10 mL of the culture medium in a humidified atmosphere of 5% CO2/95% air at 37° C. for 4-5 days until they reached 80-90% confluency. Cells were seeded into 12-well plates (1×10$^5$ cells/well containing 1 mL medium) 24 h before the beginning of the cellular uptake experiments.

The corresponding PSMA specific PET probe was added to the cells (100-150 kBq/well) and the cells were incubated at 37° C. for 1 and 2 h. 2-(Phosphonomethyl)pentanedioic acid (2-PMPA; 100 µM/well) was used for blocking studies. Thereafter, the cells were washed two times with medium (1 mL), trypsinized, harvested and the accumulated radioactivity was measured in a gamma counter (Wizard 1470, PerkinElmer, Massachusetts, USA). The cellular uptake of the novel PSMA-selective candidates and [$^{18}$F]DCFPyL obtained in experiments performed in parallel were compared. Each cellular uptake experiment was carried out in triplicate.

PET Study of PSMA-Specific Tracers in Healthy Rats

Ganglia represent an ideal tissue for the evaluation of PSMA binding imaging probes. Having a size of 1-2 mm these structures are sufficiently small to imitate metastases in a very early stage. Ganglionic PSMA is expressed by satellite glial cells, which envelop the neuronal cell bodies of the trigeminal ganglion,[25] spinal dorsal root ganglia and ganglia of the autonomic nervous system.[26] Electron microscopic studies showed that PSMA protein is mainly localized in the cell membrane of satellite cells.[27] Rat PSMA comprises 752 amino acids (vs. 750 in humans), and has about 91% homology to the human PSMA. Importantly, all amino acid residues of the active site are essentially the same as those in the human homologue with the only exception of Gly$^{548}$ in the human and Ser$^{548}$ in the rat protein, respectively[28] Furthermore, rat and human PSMA show comparable kinetic parameters for hydrolysis of N-acetylaspartylglutamate (NAAG) and similar inhibition profiles.

Notably, in contrast to tumor xenografts which rapidly change over time concerning volume, degree of vascularization and necrosis, ganglia as natural PSMA-expressing tissues remain constant over a long time. This allowed evaluation of all tested PSMA ligands in the same animal under similar conditions. (FIG. 5)

TABLE 1

Comparison of the different PSMA-specific tracers

| | SCG % ID | SCG signal-to-noise ratio | Liver % ID | Bone % ID |
|---|---|---|---|---|
| [$^{18}$F]DCFPyL (n = 6) | 20.2 ± 5.8 | 6.7 ± 2.6 | 65.3 ± 21.7 | 12.4 ± 4.3 |
| [$^{18}$F]DCFPyL + 2PMPA (n = 3) | 4.6 ± 1.8 | 3.7 ± 2.1 | 47.0 ± 7.7 | 6.1 ± 1.9 |
| [$^{18}$F]AlF-PSMA-HBED-CC (n = 3) | 36.8 ± 9.5 | 4.5 ± 1.4 | 15.5 ± 4.2† | 122.8 ± 50.2§ |
| [$^{68}$Ga]PSMA-HBED-CC (n = 3) | 41.0 ± 3.4* | 4.5 ± 0.1 | 47.0 ± 10.3 | 18.5 ± 0.6 |
| 2-MeO-[$^{18}$F]PSMA (n = 3) | 31.3 ± 10.5 | 8.2 ± 1.7 | 119.3 ± 8.3‡ | 9.9 ± 1.9 |

TABLE 1-continued

Comparison of the different PSMA-specific tracers

| | SCG % ID | SCG signal-to-noise ratio | Liver % ID | Bone % ID |
|---|---|---|---|---|
| 4-MeO-[$^{18}$F]PSMA (n = 3) | 14.4 ± 2.6 | 4.6 ± 1.3 | 29.0 ± 7.2† | 19.2 ± 2.1 |
| [$^{18}$F]PSMA-1007 (n = 3) | 94.8 ± 19.6* | 6.2 ± 1.9 | 50.7 ± 4.3 | 33.2 ± 9.5 |

Conditions: Uptake of different PSMA-specific tracers in healthy rats measured by PET. Conditions: PET scanner (Focus 220, Siemens); 57-71 MBq tracer was injected. PET scans started 60 min after injection and continued for 60 min. % ID was determined by dividing each image by the injected dose and multiplying it by body weight. Elliptical volumes of interest (VOIs) were drawn to extract mean % ID values for the rat trigeminal and superior cervical ganglia (9 mm$^3$). Background activity for calculation of signal-to-noise ratio was measured dorsal from the cervical vertebral column with a 390 mm$^3$ VOI.

[$^{18}$F]DCFPyL accumulated in peripheral ganglia with the strongest uptake in the ganglion of the trigeminal nerve (37.9±9.9% ID; n=6) measured 60-120 min after injection. In the overlay with the CT image, eight focal accumulations of radioactivity were detected in the interventricular forming between the cervical vertebrae, an anatomical localization assigned to the spinal dorsal root ganglia. High tracer uptake was also visible in the stellate ganglion, salivary glands and heart (FIG. 5A). In the shoulder joint, [$^{18}$F]DCFPyL accumulation seemed to be restricted to the articular cartilage (FIG. 5A). The superior cervical ganglion (SCG; volume approx. 9 mm$^3$) was a simply recognizable structure fitting in the 7 cm axial field of view of the Focus 220 scanner together with the spinal ganglia, heart and the frontal part of the liver. It was sufficiently distant from bone structures. That allowed quantification of the SCG radioactivity accumulation even if tracer defluorination resulted in high $^{18}$F$^-$ bone uptake. We therefore used the SCG as a reference structure with a mean (±standard deviation) [$^{18}$F]DCFPyL uptake of 20.2±5.8% ID (range 13.3-29.6% ID; n=6) and a signal-to-noise ratio of 6.7±2.6 (Table 1). The co-application of the PSMA-inhibitor 2-PMPA strongly decreased [$^{18}$F]DCFPyL accumulation in all above-mentioned PSMA-positive tissues (FIG. 5B, Table 1; decrease from 20.2±5.8 to 4.6±1.8% ID in the SCG, n=3). At the same time tracer accumulation in the liver remained at the same level.

Uptake of 2-MeO-[$^{18}$F]PSMA in SCG was higher than for [$^{18}$F]DCFPyL (31.3±10.5 vs. 20.2±5.8% ID) (FIG. 5B). Together with the comparable unspecific uptake this resulted in a higher signal-to-noise ratio of 8.2±1.7% ID. The bone uptake of the tracer was slightly lower in comparison to [$^{18}$F]DCFPyL. Liver accumulation of 2-MeO-[$^{18}$F]PSMA was rather high. In contrast to the 2-methoxy substituted tracer, 4-MeO-[$^{18}$F]PSMA showed a low uptake and signal-to-noise ratio in the SCG (14.4±2.6% ID and 4.6±1.3, respectively) (FIG. 5C, Table 1). Interestingly, liver uptake of the tracer was significantly lower and the bone uptake was higher as that of 2-MeO-[$^{18}$F]PSMA (29.0±7.2 vs. 119.3±8.3% ID and 19.2±2.1 vs. 9.9±1.9% ID, respectively).

While accumulation of [$^{68}$Ga]Ga-PSMA-HBED-CC in the SCG was significantly higher than that of [$^{18}$F]DCFPyL (41.0±3.4% ID), high unspecific uptake in non-target target tissue resulted in a lower signal-to-noise ratio of 4.5±0.1 (FIG. 5B). The image resolution was lower compared to that of [$^{18}$F]DCFPyL, presumably, owing to the higher β$^+$-energy of $^{68}$Ga in comparison to $^{18}$F (1.9 vs. 0.6 MeV).

Next, [$^{18}$F]AlF-PSMA-HBED-CC was studied (FIG. 5E). Surprisingly, despite the previously described stability of the tracer, a high radioactivity uptake in bones (122.8±50.2% ID) indicated significant in vivo defluorination. The observed instability substantially limits the applicability of [$^{18}$F]AlF-PSMA-HBED-CC in clinical practice.

Among all tested PET tracers [$^{18}$F]PSMA-1007 demonstrated the highest uptake in the SCG (FIG. 5E). A high unspecific uptake, however, led to a signal-to-noise ratio in the range comparable to [$^{18}$F]DCFPyL (6.2±1.9 vs. 6.7±2.6% ID for [$^{18}$F]PSMA-1007 and

[$^{18}$F]DCFPyL, respectively) (FIG. 5E, Table 1). Thus, bone uptake of [$^{18}$F]PSMA-1007 was higher and liver uptake was somewhat lower as for [$^{18}$F]DCFPyL (33.2±9.5 and 50.7±4.3% ID for [$^{18}$F]PSMA-1007 and [$^{18}$F]DCFPyL, respectively).

Example 12: PET Evaluation of [$^{18}$F]1 and [$^{18}$F]2 in Healthy Rats in Comparison to Known PSMA Specific Tracers Animals: Experiments were carried out in accordance with the EU directive 2010/63/EU for animal experiments and the German Animal Welfare Act (TierSchG, 2006), and were approved by regional authorities (LANUV NRW). Long Evans rats (250-590 g body weight) were used for this study. Rats were housed in pairs in individually ventilated cages (NexGen EcoFlo, cages RAT1800 with 1805 cm$^2$ floor space and 41 cm height; Allentown Inc., Allentown, N.J., USA) under controlled ambient conditions (22±1° C. and 55±5% relative humidity) on an inversed 12 hour light/dark schedule (lights on 9:00 p.m.-9:00 a.m.). Food and water were available at all times. Three rats received two, and one rat received three different tracers. The other seven rats were measured with one tracer only. Each tracer was measured in three animals.

PET-imaging: Prior to PET measurements with PET probes, animals were anesthetized (initial dosage: 5% isoflurane in 02/air (3:7), then reduction to 2%), and a catheter for tracer injection was inserted into the lateral tail vein. Rats were placed on an animal holder (Medres, Cologne, Germany), and fixed with a tooth bar in a respiratory mask. Dynamic PET scans in a list mode were performed using a Focus 220 micro PET scanner (CTI-Siemens, Germany) with a resolution at a center of field of view of 1.4 mm. Data acquisition started with tracer injection (66±14 MBq in 0.5 mL i.v.), continued for 120 min and was followed by a 10 min transmission scan using a $^{57}$Co point source. For blocking studies 2-(phosphonomethyl)pentanedioic acid (2-PMPA; 23 mg/kg) was added directly to a radiotracer solution. Breathing rate was monitored and kept around 60/min by adjusting isoflurane concentration (1.5-2.5%). Body temperature was maintained at 37° C. by a feedback-controlled system. Following Fourier rebinning, data were reconstructed using an iterative OSEM3D/MAP procedure78 including attenuation and decay correction in two different ways: 1) 28 frames (2×1 min; 2×2 min, 6×4 min, 18×5 min) for compilation of regional time activity curves; 2) 4 frames (4×30 min) for visual display. Resulting voxel sizes were always 0.38×0.38×0.79 mm.

Data analysis was performed using the software VINCI.79 Images were Gauss filtered (1 mm FWHM), and % ID was determined by dividing each image by the injected dose and multiplying the result by body weight times 100. Mean % ID values were extracted from each of the 28 frames and plotted over time.

First Clinical Experience with [$^{18}$F]1

Owing to the favorable imaging properties of 2-MeO-[$^{18}$F]PSMA in rats a small pilot study with this tracer in 10 patients was conducted. All patients were examined with both [$^{68}$Ga]Ga-PSMA-HBED-CC and 2-MeO-[$^{18}$F]PSMA PET CT. In each case, both PET/CT scans were carried out within three weeks. Accordingly, six patients exhibited at least one PSMA-positive suspicious lesion detected by [$^{68}$Ga]Ga-PSMA-HBED-CC and/or 2-MeO-[$^{18}$F]PSMA PET/CT (FIG. 6). In four patients, at least one additional PSMA-positive lesion using 2-MeO-[$^{18}$F]PSMA compared to the corresponding [$^{68}$Ga]Ga-PSMA-HBED-CC image was identified (FIG. 6B). In one patient inconspicuous in the [$^{68}$Ga]Ga-PSMA-HBED-CC scan, a PSMA-positive lesion was discovered by 2-MeO-[$^{18}$F]PSMA PET/CT (FIG. 6C).

In the subsequent larger study, 124 patients with biochemical recurrence (BCR) of PCa were examined. In this patient cohort a sensitivity of 83.0% was determined for 2-MeO-[$^{18}$F]PSMA compared to 79.1% and 74.2% determined earlier for [$^{18}$F]DCFPyL and [$^{68}$Ga]Ga-PSMA-HBED-CC, respectively.

Example 13: PSMA-PET Imaging of Patients with Biochemical Recurrence of Prostate Cancer The study was conducted in accordance with the Institutional Review Board. All patients gave written informed consent to PET imaging and inclusion of their data in a retrospective analysis. All procedures were performed in compliance with the regulations of the responsible local authorities (District Administration of Cologne, Germany).

All measurements with [$^{68}$Ga]Ga-PSMA-HBED-CC and [$^{18}$F]-2-MeO-PSMA were carried out as described in the literature.[14a, 15]

LITERATURE

[1] B. Barnes, K. Kraywinkel, *Bericht zum Krebsgeschehen in Deutschland* 2016 2017.

[2] P. J. Effert, R. Bares, S. Handt, J. M. Wolff, U. Bull, G. Jakse, *The Journal of urology* 1996, 155, 994.

[3] S. Schwarzenbock, M. Souvatzoglou, B. J. Krause, *Theranostics* 2012, 2, 318.

[4] a) M. Farsad, R. Schiavina, P. Castellucci, C. Nanni, B. Corti, G. Martorana, R. Canini, W. Grigioni, S. Boschi, M. Marengo, *J. Nucl. Med.* 2005, 46, 1642; b) S. N. Reske, N. M. Blumstein, G. Glatting, *Der Urologe* 2006, 45, 707; c) O. Schillaci, F. Calabria, M. Tavolozza, C. Ciccio, M. Carlani, C. R. Caracciolo, R. Danieli, A. Orlacchio, G. Simonetti, *Nucl. Med Commun.* 2010, 31, 39.

[5] a) T. Pan, L. Gao, G. Wu, G. Shen, S. Xie, H. Wen, J. Yang, Y. Zhou, Z. Tu, W. Qian, *Biochem. Biophys. Res. Commun.* 2015, 456, 452; b) Q. Wang, R. A. Hardie, A. J. Hoy, M. van Geldermalsen, D. Gao, L. Fazli, M. C. Sadowski, S. Balaban, M. Schreuder, R. Nagarajah, J. J. Wong, C. Metierre, N. Pinello, N. J. Otte, M. L. Lehman, M. Gleave, C. C. Nelson, C. G. Bailey, W. Ritchie, J. E. Rasko, J. Holst, *J. Pathol.* 2015, 236, 278.

[6] D. M. Schuster, C. Nanni, S. Fanti, *J. Nucl. Med* 2016, 57, 61S.

[7] a) R. Amzat, P. Taleghani, D. L. Miller, J. J. Beitler, L. M. Bellamy, J. A. Nye, W. Yu, B. Savir-Baruch, A. O. Osunkoya, Z. Chen, W. F. Auffermann, M. M. Goodman, D. M. Schuster, *Mol. Imaging Biol.* 2013, 15, 633; b) K. Kairemo, N. Rasulova, K. Partanen, T. Joensuu, *Biomed Res Int* 2014, 2014, 305182; c) C. Nanni, R. Schiavina, S. Boschi, V. Ambrosini, C. Pettinato, E. Brunocilla, G. Martorana, S. Fanti, *Eur. J. Nucl. Med. Mol. Imaging* 2013, 40 Suppl 1, S11; d) C. Nanni, R. Schiavina, E. Brunocilla, M. Borghesi, V. Ambrosini, L. Zanoni, G. Gentile, V. Vagnoni, D. Romagnoli, G. Martorana, S. Fanti, *Clin. Genitourin. Cancer* 2014, 12, 106; e) D. M. Schuster, B. Savir-Baruch, P. T. Nieh, V. A. Master, R. K. Halkar, P. J. Rossi, M. M. Lewis, J. A. Nye, W. Yu, F. D. Bowman, M. M. Goodman, *Radiology* 2011, 259, 852; f) J. Sorensen, R. Owenius, M. Lax, S. Johansson, *Eur. J. Nucl. Med Mol. Imaging* 2013, 40, 394; g) H. Suzuki, Y. Inoue, H. Fujimoto, J. Yonese, K. Tanabe, S. Fukasawa, T. Inoue, S. Saito, M. Ueno, A. Otaka, Jpn. *J. Clin. Oncol.* 2016, 46, 152; h) B. Turkbey, E. Mena, J. Shih, P. A. Pinto, M. J. Merino, M. L. Lindenberg, M. Bernardo, Y. L. McKinney, S. Adler, R. Owenius, P. L. Choyke, K. A. Kurdziel, *Radiology* 2014, 270, 849.

[8] FDA approves new diagnostic imaging agent to detect recurrent prostate cancer, https://www.fda.gov/NewsEvents/Newsroom/PressAnnouncements/ucm503920.htm, downloaded on Dec. 27, 2017

[9] J. Ren, L. Yuan, G. Wen, J. Yang, *Acta Radiol.* 2016, 57, 487.

[10] a) S. Perner, M. D. Hofer, R. Kim, R. B. Shah, H. Li, P. Möller, R. E. Hautmann, J. E. Gschwend, R. Kuefer, M. A. Rubin, *Hum. Pathol.*, 38, 696; b) J. S. Ross, C. E. Sheehan, H. A. Fisher, R. P. Kaufman, P. Kaur, K. Gray, I. Webb, G. S. Gray, R. Mosher, B. V. Kallakury, *Clin. Cancer Res.* 2003, 9, 6357; c) S. D. Sweat, A. Pacelli, G. P. Murphy, D. G. Bostwick, *Urology,* 52, 637.

[11] C. Parker, S. Gillessen, A. Heidenreich, A. Horwich, *Ann. Oncol.* 2015, 26, v69.

[12] E. M. Uchio, M. Aslan, C. K. Wells, J. Calderone, J. Concato, *Arch. Intern. Med.* 2010, 170, 1390.

[13] a) V. Bouvet, M. Wuest, J. J. Bailey, C. Bergman, N. Janzen, J. F. Valliant, F. Wuest, *Mol. Imaging Biol.* 2017, 19, 923; b) J. Cardinale, M. Schafer, M. Benesova, U. Bauder-Wust, K. Leotta, M. Eder, O. C. Neels, U. Haberkorn, F. L. Giesel, K. Kopka, *J. Nucl. Med.* 2017, 58, 425; c) Y. Chen, M. Pullambhatla, C. A. Foss, Y. Byun, S. Nimmagadda, S. Senthamizhchelvan, G. Sgouros, R. C. Mease, M. G. Pomper, *Clin. Cancer Res.* 2011, 17, 7645; d) C. A. Foss, R. C. Mease, H. Fan, Y. Wang, H. T. Ravert, R. F. Dannals, R. T. Olszewski, W. D. Heston, A. P. Kozikowski, M. G. Pomper, *Clin. Cancer Res.* 2005, 11, 4022; e) J. Kelly, A. Amor-Coarasa, A. Nikolopoulou, D. Kim, C. Williams, Jr., S. Ponnala, J. W. Babich, *Eur. J. Nucl. Med. Mol. Imaging* 2017, 44, 647; f) N. Malik, H. J. Machulla, C. Solbach, G. Winter, S. N. Reske, B. Zlatopolskiy, *Appl. Radiat. Isot.* 2011, 69, 1014; g) N. Malik, B. Zlatopolskiy, H.-J. Machulla, S. N. Reske, C. Solbach, *J. Label. Compd Radiopharm.* 2012, 55, 320; h) X. Yang, R. C. Mease, M. Pullambhatla, A. Lisok, Y. Chen, C. A. Foss, Y. Wang, H. Shallal, H. Edelman, A. T. Hoye, G. Attardo, S. Nimmagadda, M. G. Pomper, *J. Med. Chem.* 2016, 59, 206.

[14] a) F. Dietlein, C. Kobe, S. Neubauer, M. Schmidt, S. Stockter, T. Fischer, K. Schomacker, A. Heidenreich, B. D. Zlatopolskiy, B. Neumaier, A. Drzezga, M. Dietlein, *J. Nucl. Med.* 2017, 58, 947; b) X. Li, S. P. Rowe, J. P. Leal, M. A. Gorin, M. E. Allaf, A. E. Ross, K. J. Pienta, M. A. Lodge, M. G. Pomper, *J. Nucl. Med.* 2017, 58, 942; c) S. P. Rowe, M. A. Gorin, H. J. Hammers, M. G. Pomper, M. E. Allaf, M. S. Javadi, *Clin Nucl Med* 2016, 41, 83; d) S.

P. Rowe, M. Mana-Ay, M. S. Javadi, Z. Szabo, J. P. Leal, M. G. Pomper, K. J. Pienta, A. E. Ross, M. A. Gorin, *Clin. Genitourin. Cancer* 2016, 14, e115; e) Z. Szabo, E. Mena, S. P. Rowe, D. Plyku, R. Nidal, M. A. Eisenberger, E. S. Antonarakis, H. Fan, R. F. Dannals, Y. Chen, R. C. Mease, M. Vranesic, A. Bhatnagar, G. Sgouros, S. Y. Cho, M. G. Pomper, *Mol. Imaging Biol.* 2015, 17, 565; f) M. Wondergem, F. M. van der Zant, R. J. J. Knol, S. V. Lazarenko, J. Pruim, I. J. de Jong, *J. Nucl. Med* 2017, 58, 1797.

[15] M. Dietlein, C. Kobe, G. Kuhnert, S. Stockter, T. Fischer, K. Schomacker, M. Schmidt, F. Dietlein, B. D. Zlatopolskiy, P. Krapf, R. Richarz, S. Neubauer, A. Drzezga, B. Neumaier, *Mol. Imaging Biol.* 2015, 17, 575.

[16] a) B. Drennen, J. A. Scheenstra, J. L. Yap, L. Chen, M. E. Lanning, B. M. Roth, P. T. Wilder, S. Fletcher, *Chem Med Chem* 2016, 11, 827; b) T. Ehara, O. Irie, T. Kosaka, T. Kanazawa, W. Breitenstein, P. Grosche, N. Ostermann, M. Suzuki, S. Kawakami, K. Konishi, *ACS Med Chem. Lett.* 2014, 5, 787.

[17] B. Neumaier, B. Zlatopolskiy, R. Richarz, P. Krapf, *Method for the production of 18f-labeled active esters and their application exemplified by the preparation of a psma-specific pet-tracer*, WO2016030329 A1, 2016.

[18] V. Bouvet, M. Wuest, H. S. Jans, N. Janzen, A. R. Genady, J. F. Valliant, F. Benard, F. Wuest, *EJNMMI research* 2016, 6, 40.

[19] H. T. Ravert, D. P. Holt, Y. Chen, R. C. Mease, H. Fan, M. G. Pomper, R. F. Dannals, *J Labelled Comp Radiopharm* 2016, 59, 439.

[20] M. Eder, O. Neels, M. Muller, U. Bauder-Wust, Y. Remde, M. Schafer, U. Hennrich, M. Eisenhut, A. Afshar-Oromieh, U. Haberkorn, K. Kopka, *Pharmaceuticals (Basel)* 2014, 7, 779.

[21] S. Boschi, J. T. Lee, S. Beykan, R. Slavik, L. Wei, C. Spick, U. Eberlein, A. K. Buck, F. Lodi, G. Cicoria, J. Czernin, M. Lassmann, S. Fanti, K. Herrmann, *Eur. J. Nucl. Med Mol. Imaging* 2016, 43, 2122.

[22] J. Cardinale, R. Martin, Y. Remde, M. Schafer, A. Hienzsch, S. Hubner, A. M. Zerges, H. Marx, R. Hesse, K. Weber, R. Smits, A. Hoepping, M. Muller, O. C. Neels, K. Kopka, *Pharmaceuticals (Basel)* 2017, 10, 77.

[23] F. L. Giesel, B. Hadaschik, J. Cardinale, J. Radtke, M. Vinsensia, W. Lehnert, C. Kesch, Y. Tolstov, S. Singer, N. Grabe, S. Duensing, M. Schafer, O. C. Neels, W. Mier, U. Haberkorn, K. Kopka, C. Kratochwil, *Eur. J. Nucl. Med Mol. Imaging* 2017, 44, 678.

[24] P. F. Jackson, D. C. Cole, B. S. Slusher, S. L. Stetz, L. E. Ross, B. A. Donzanti, D. A. Trainor, *J. Med Chem.* 1996, 39, 619.

[25] J.-P. Vit, L. Jasmin, A. Bhargava, P. T. Ohara, *Neuron glia biology* 2006, 2, 247.

[26] K. R. Jessen, R. Mirsky, *Nat. Rev. Neurosci.* 2005, 6, 671.

[27] U. V. Berger, R. E. Carter, M. McKee, J. T. Coyle, *J. Neurocytol.* 1995, 24, 99.

[28] M. Rovensk, K. Hlouchová, P. Šácha, P. Mlčochová, V. Horák, J. Zámečník, C. Bařinka, J. Konvalinka, *The Prostate* 2008, 68, 171.

BRIEF DESCRIPTION OF THE DRAWINGS

FIG. 6 is provided in FIGS. 6a and 6b. Left column: [$^{68}$Ga]Ga-PSMA-HBED-CC PET-data, right column: 2-MeO-[$^{18}$F]PMSA PET-data in the same patient. First row: Maximal intensity projections of the PET-data (darker black color reflects higher tracer uptake). Second row: Axial slices (caudal aspect) of the PET/CT fusion images (overlay of PET-data on the CT data). PET-tracer uptake displayed in "hot metal" (brighter yellow color reflects higher tracer uptake). Bl: Bladder, Bo: Bowel, K: Kidney, L: Liver, Sa: Salivary glands, Sp: Spleen, Tu: Suspected tumor, U: Ureter, R: Right side, L: Left side.

Figure 1:
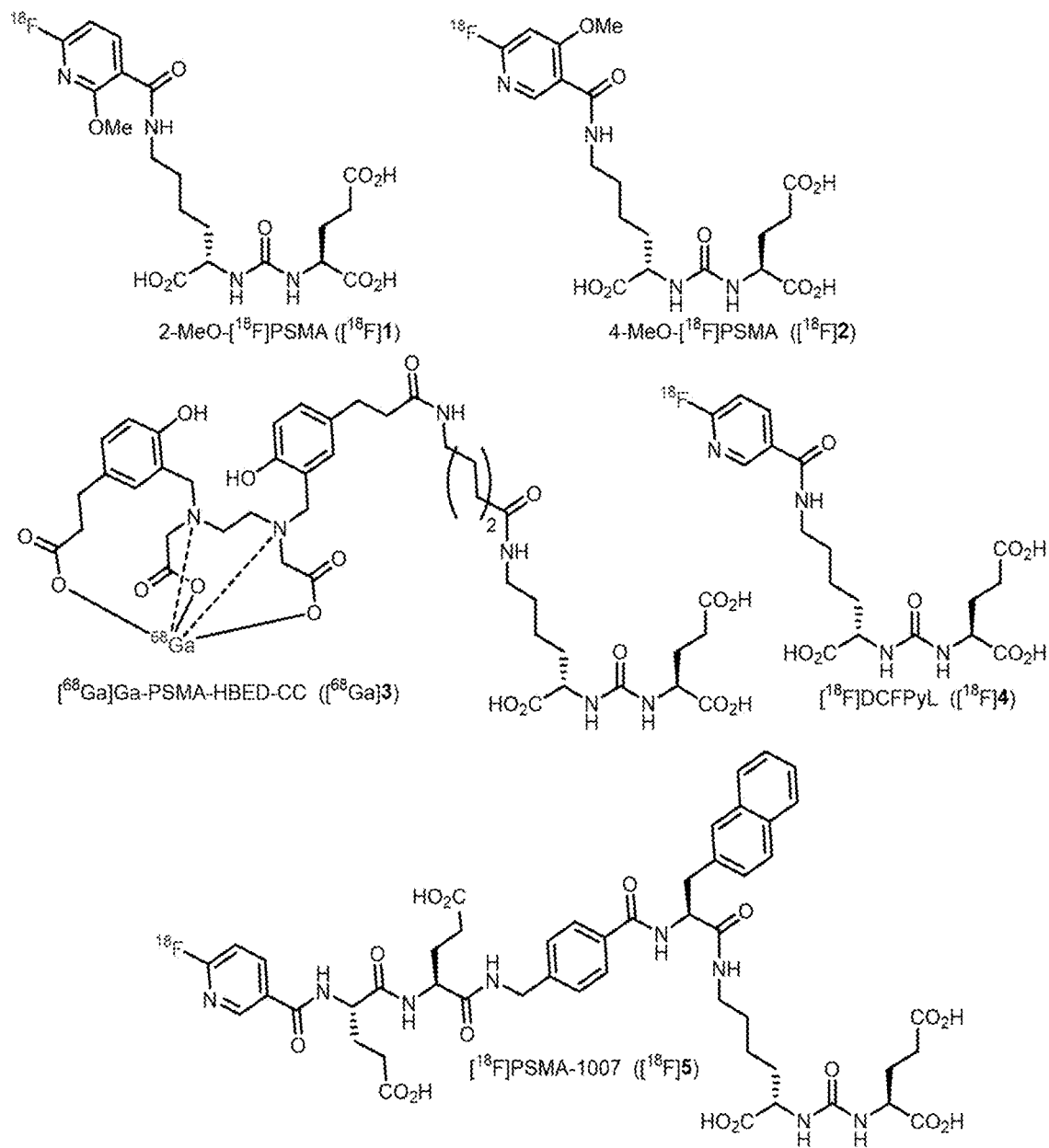
FIG. 1: Structures of PSMA-specific PET-Ligands used in this study.
Figure 2:
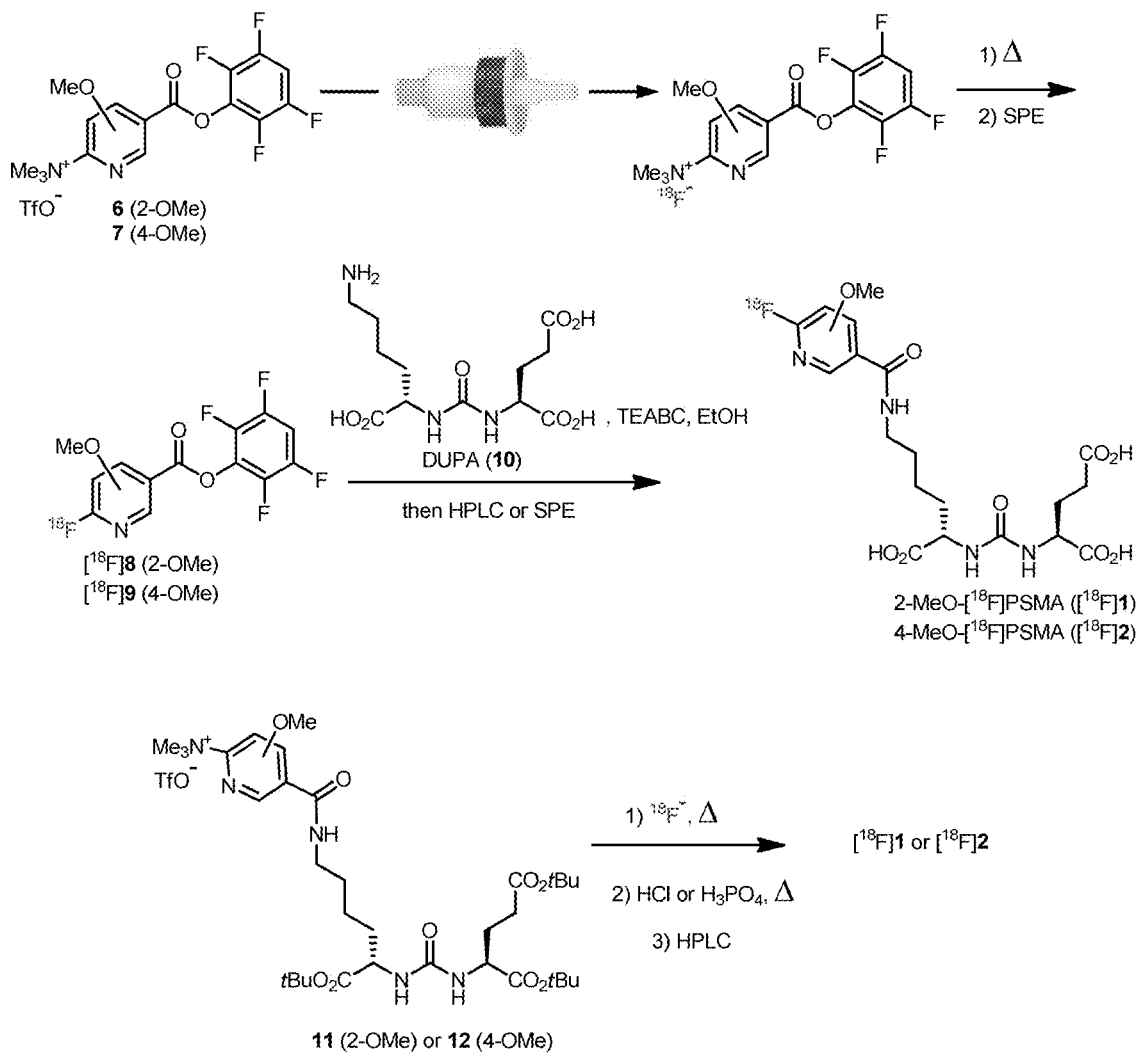
FIG. 2: Preparation of the novel PSMA specific probes, [$^{18}$F]1 and [$^{18}$F]2.
Figure 3:
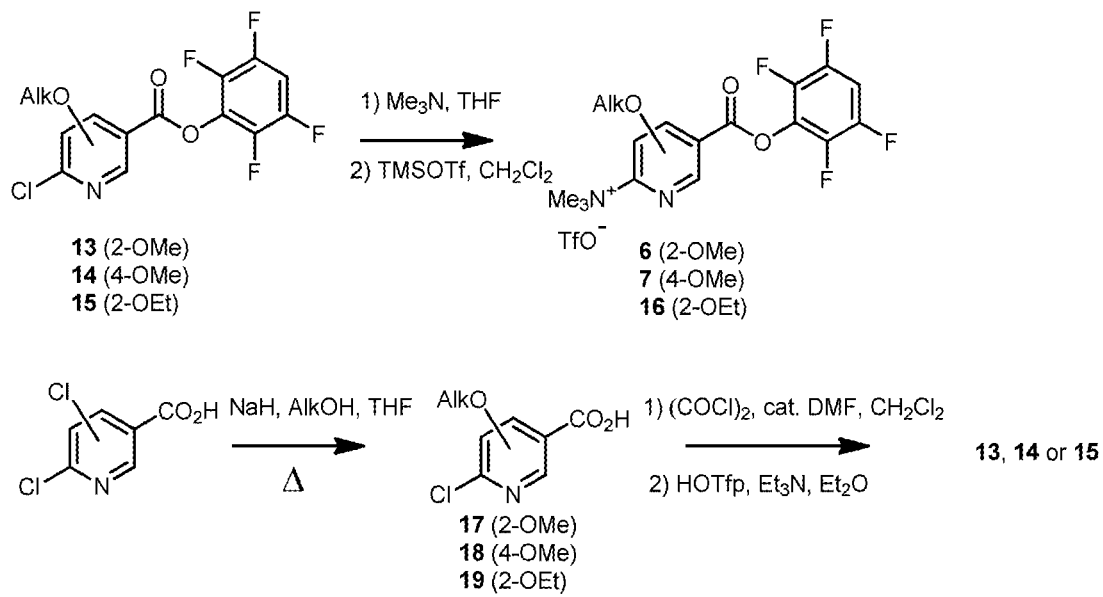
FIG. 3: Synthesis of precursors 8, 9 and 16 for radiolabeling.
Figure 4:
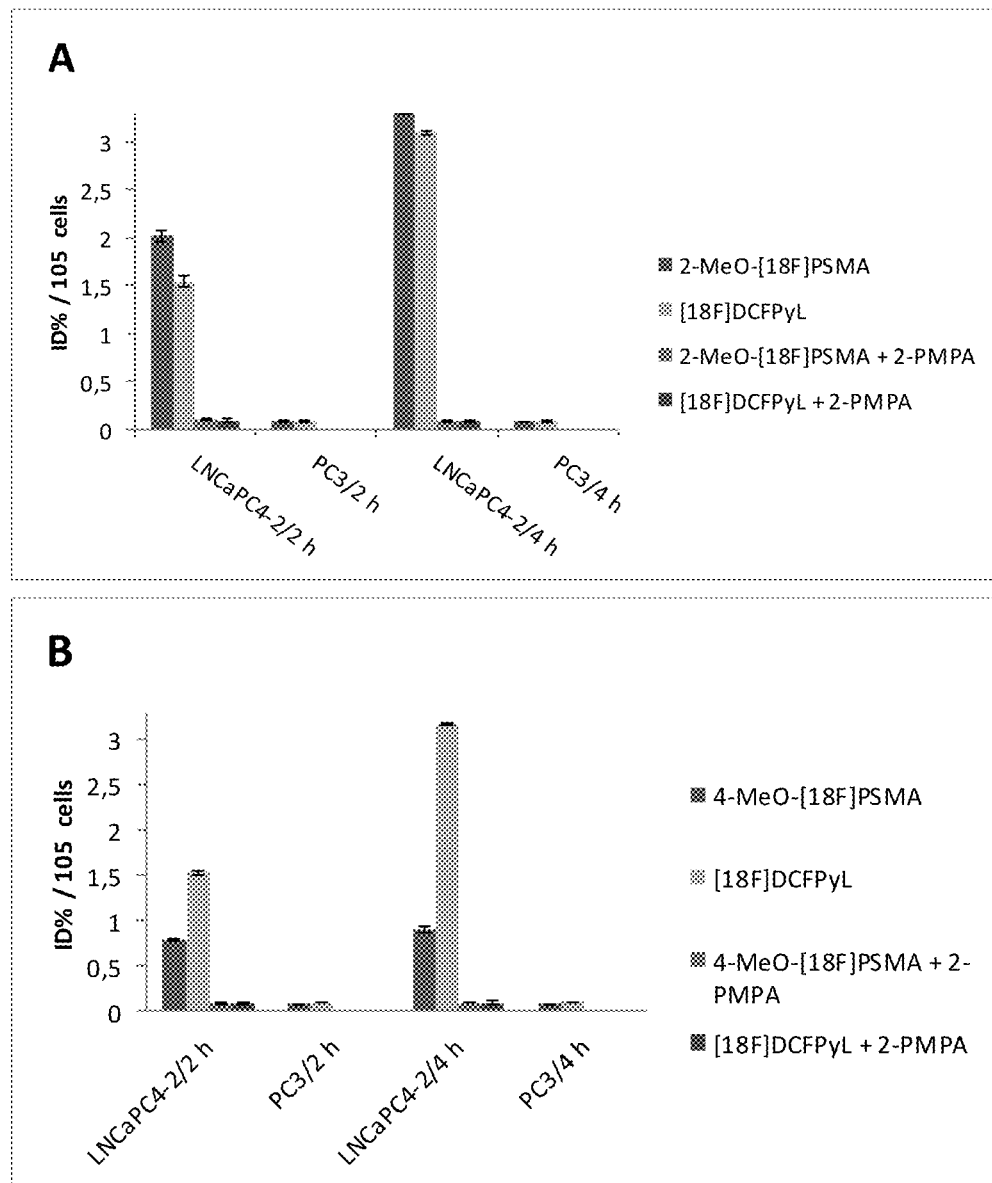
FIG. 4: Cellular uptake of 2-MeO— and 4-MeO-[$^{18}$F] PSMA (A and B, respectively), and [$^{18}$F]DCFPyL in PSMA$^+$ LNCaP C4-2 and PSMA$^-$ prostate tumor cells. Data of cellular uptakes [$^{18}$F]DCFPyL carried out in parallel with those of 2-MeO— and 4-MeO-[$^{18}$F]PSMA are presented.
Figure 5:
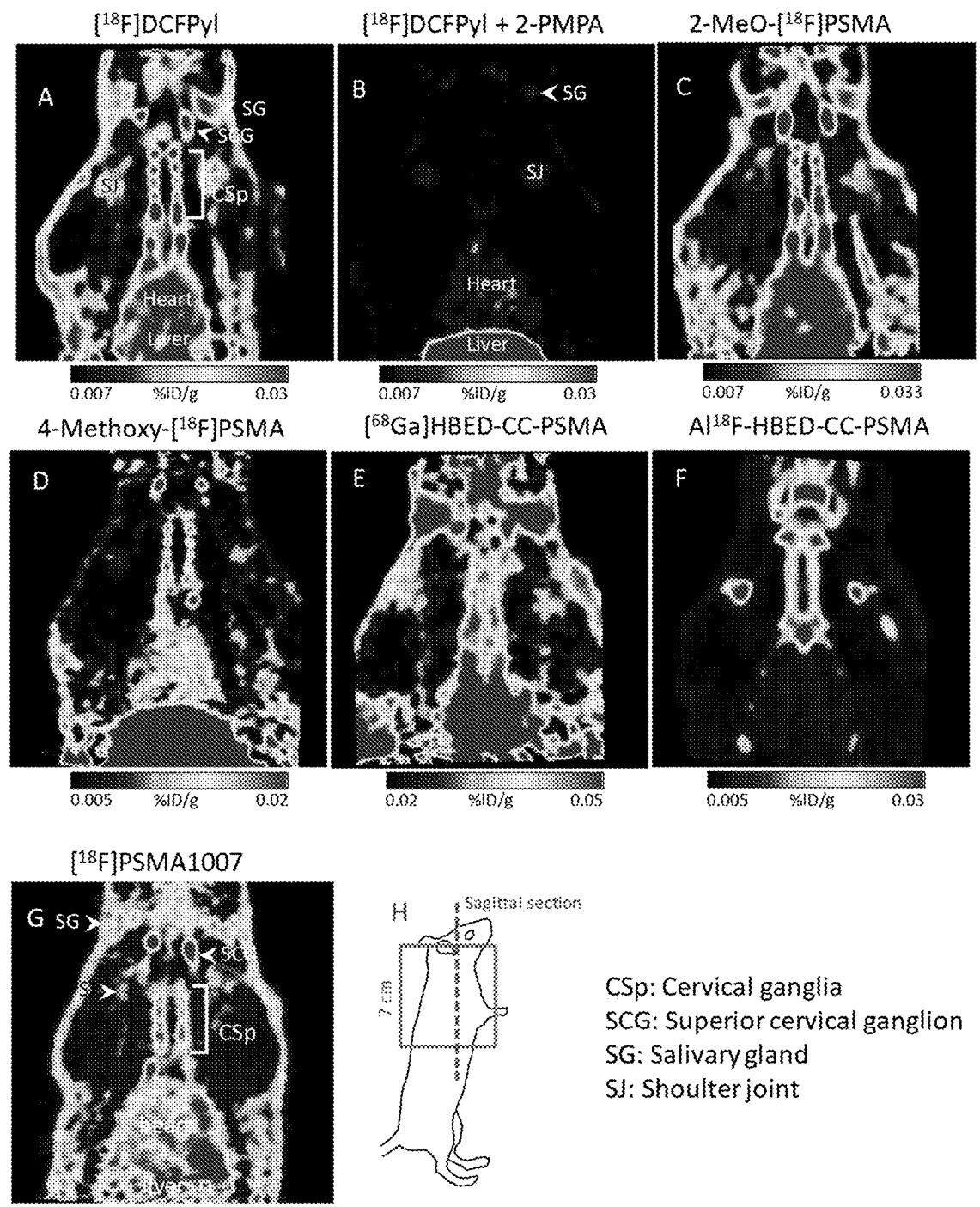
FIG. 5: Uptake of different PSMA-specific tracers in healthy rats measured by PET. Conditions: PET scanner (Focus 220, Siemens); 57-71 MBq tracer was injected. PET scans started 60 min after injection and continued for 60 min. A: [$^{18}$F]DCFPyL; B: [$^{18}$F]DCFPyL+2-PMPA (23 mg/kg); C: 2-MeO-[$^{18}$F]PSMA; D: 4-MeO-[$^{18}$F]PSMA, E: [$^{68}$Ga]Ga-PSMA-HBED-CC, F: [$^{18}$F]AlF-PSMA-HBED-CC G: [$^{18}$F]PSMA-1007 H: Shown sagittal section and list of abbreviations.
Figure 6A:
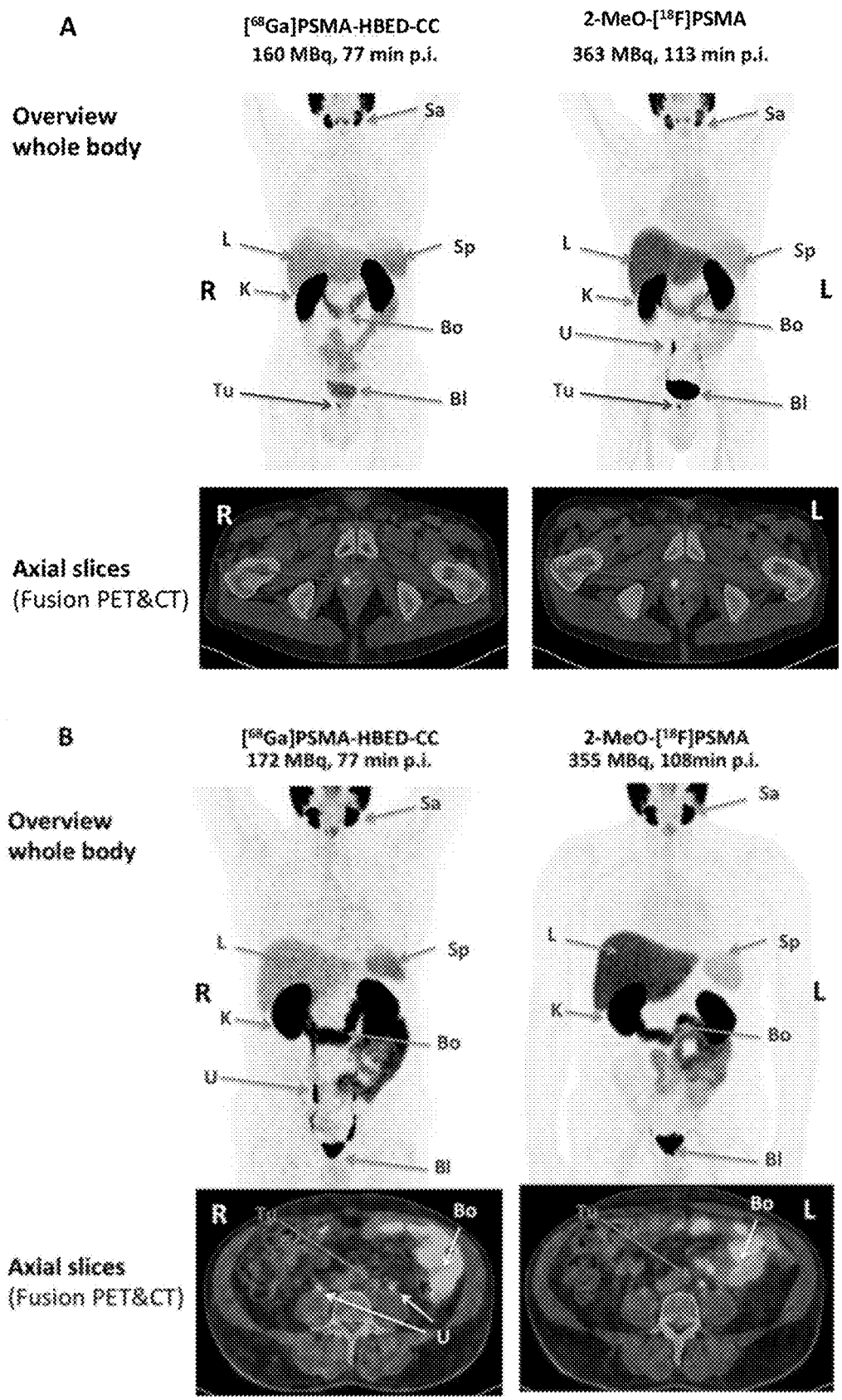
FIG. 6.
Figure 6B:
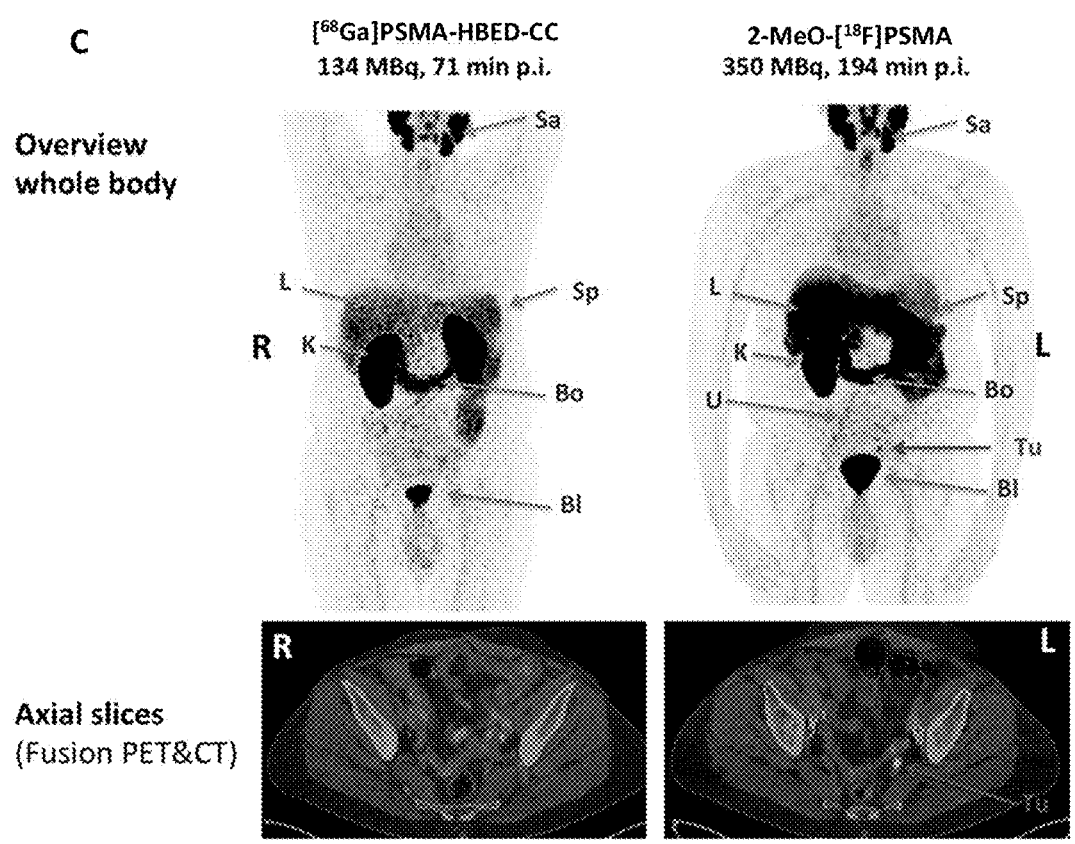
Figure 7:
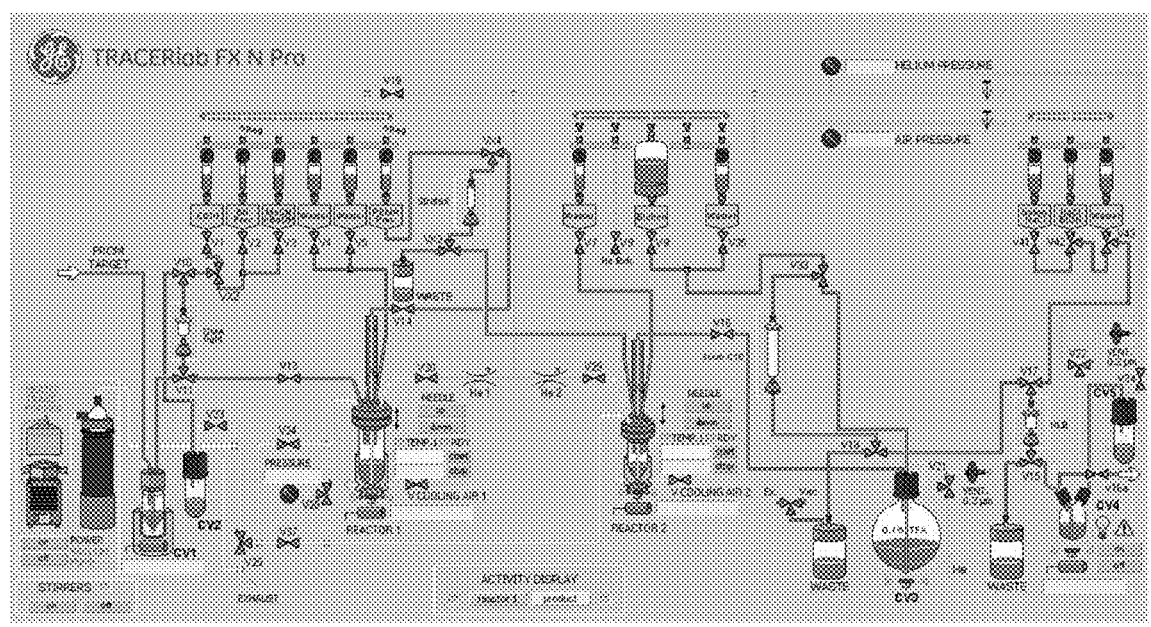
FIG. 7: Layout of 2-MeO-[$^{18}$F]PSMA synthesis on FX— N-Pro synthesis module.
Figure 8:
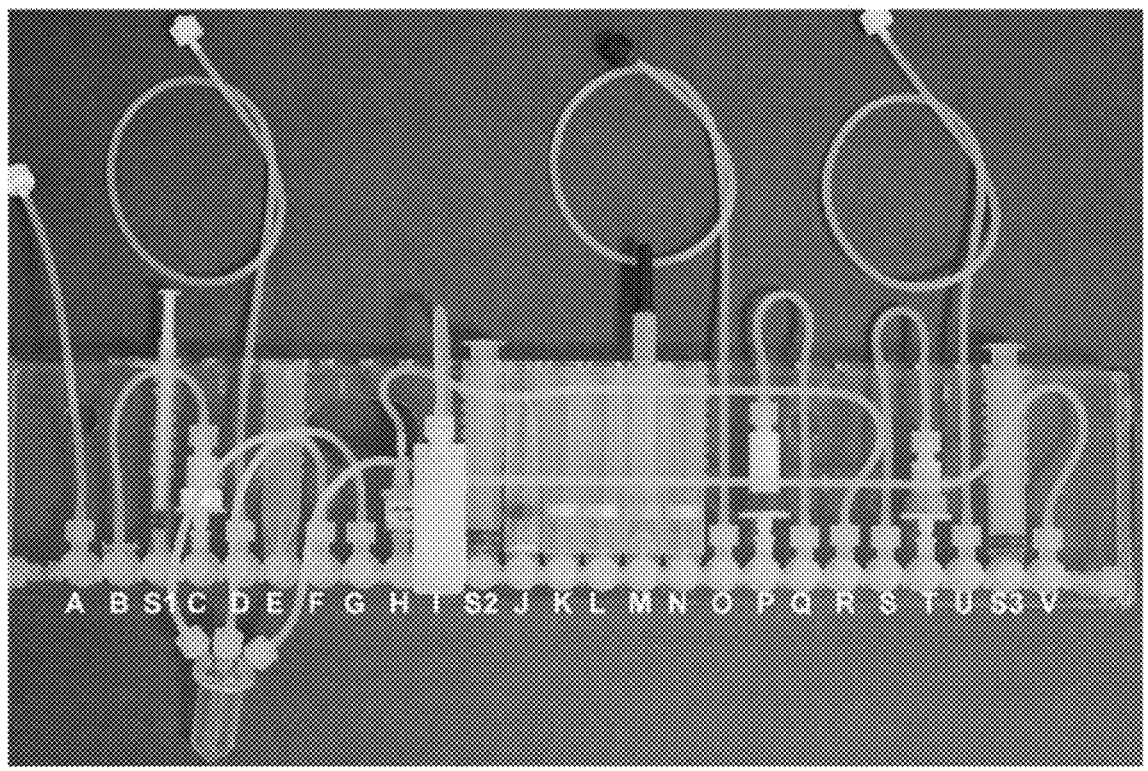
FIG. 8: Cassette for the production of [$^{18}$F]1 on FASTab synthesis module (GE).
Figure 9:
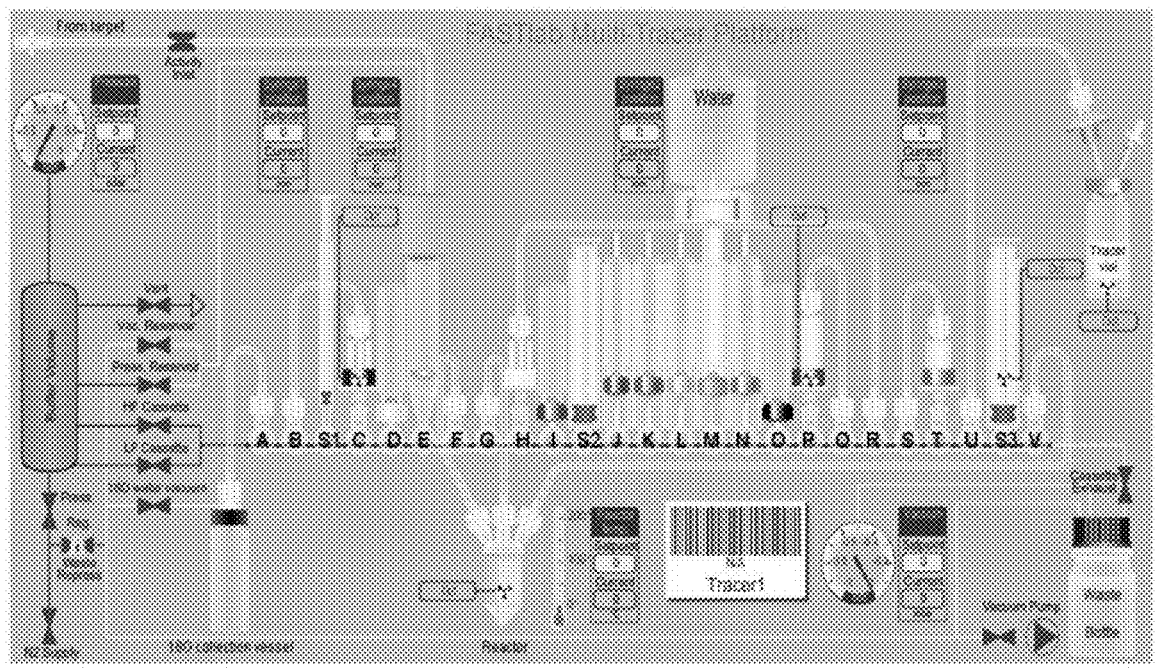
FIG. 9: Production of [$^{18}$F]1 on FASTab synthesis module (GE).

The invention claimed is:

1. A compound of formula (I):

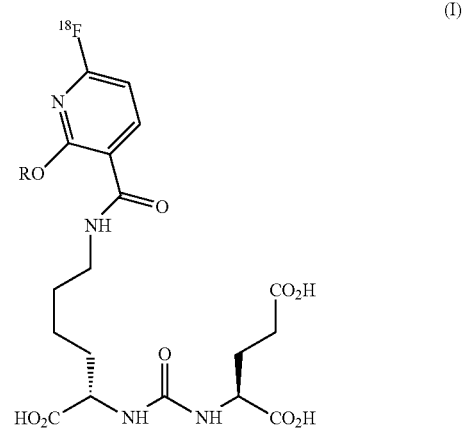

wherein R is $C_1$-$C_{10}$ substituted or unsubstituted alkyl, or $C_5$-$C_{12}$ unsubstituted or substituted aryl or heteroaryl.

2. The compound of formula (I) according to claim 1 wherein R is C1-C4 substituted or unsubstituted alkyl.

3. The compound of formula (I) according to claim 1 wherein R is C1-C3 substituted or unsubstituted alkyl.

4. The compound of formula (I) according to claim 1 wherein R is methyl.

5. A method for imaging of a PSMA-positive organ or tissue or both in a subject, comprising administering to said subject the compound of formula (I) according to claim 1 and obtaining and image of said organ or tissue or both.

6. The method according to claim 5, wherein said subject has a pathological condition that is selected from the group consisting of cancer, prostate cancer, re-endothelialization, neuropathic pain and atherosclerosis.

7. A method for staging a pathological or physiological condition associated with one or more PSMA-positive organs or tissues or both of a subject, comprising administering to said subject the compound of formula (I) according to claim 1 and staging said pathological or physiological condition.

8. The method according to claim 7, wherein said subject has a pathological condition that is selected from the group consisting of cancer, prostate cancer, reendothelialization, neuropathic pain and atherosclerosis.

9. A method of making a compound of formula (I) according to claim 1 from a compound of formula II and Lys-C(O)-Glu comprising:

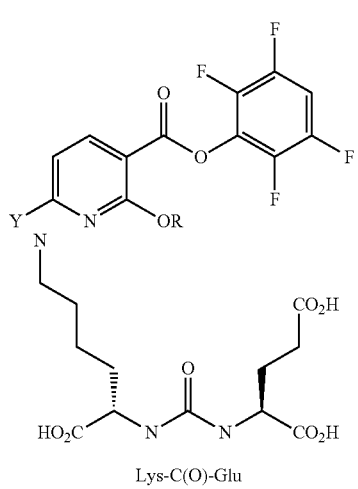

Lys-C(O)-Glu

Y is Me$_3$N$^+$Z$^-$ or

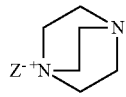

Z$^-$ is CF$_3$SO$_3$ or CF$_3$CO$_2$

R is C$_1$-C$_{10}$ substituted or unsubstituted alkyl, or C$_5$-C$_{12}$ unsubstituted or substituted aryl or heteroaryl, a) providing an aqueous solution of [$^{18}$F]fluoride;
b) loading of [$^{18}$F]fluoride onto an anion exchange resin;
c) washing the anion exchange resin;
d) drying the resin with flow of air or inert gas;
e) elution of [$^{18}$F]fluoride with a solution of a compound of formula (II) in a polar aprotic solvent;
f) if the elution was carried out by a C$_2$-C$_6$ alcohol as the solvent, then diluting the reaction mixture with a polar aprotic solvent;
g) heating the resulting solution at 30-70° C. for 1-30 min which furnishes a crude of a compound of formula [$^{18}$F]III;

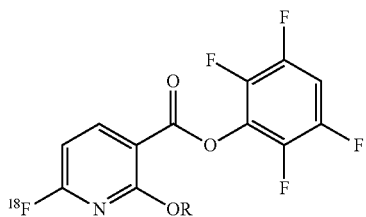

wherein R is as defined for formula II, h) purification of the compound of formula [$^{18}$F]III reversed phase solid phase extraction (RP SPE) as follows: dilution of the above mixture with H$_2$O, loading the resulting solution on a RP SPE cartridge, washing the cartridge with H$_2$O, elution of the purified compound of formula [$^{18}$F]III with a C$_2$-C$_6$ alcohol;
i) elution of the purified compound of formula [$^{18}$F]III directly to a solution of Lys-C(O)-Glu and a base in an anhydrous C$_2$-C$_6$ alcohol;
j) heating the resulting solution at 30-70° C. for 1-30 min;
k) purification of the resultant crude compound of formula I by RP SPE or alternatively RP HPLC; and
l) optionally formulation.

10. A method of making a compound of formula (I) according to claim 1 from a compound of formula (IV) comprising:

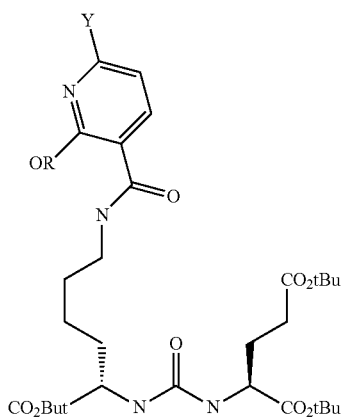

wherein
Y is Me$_3$N$^+$Z$^-$ or

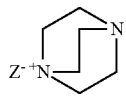

Z$^-$ is CF$_3$SO$_3$ or CF$_3$CO$_2$
R is C$_1$-C$_{10}$ substituted or unsubstituted alkyl, or C$_5$-C$_{12}$ unsubstituted or substituted aryl or heteroaryl,
a) providing an aqueous solution of [$^{18}$F]fluoride;
b) loading of [$^{18}$F]fluoride onto an anion exchange resin;
c) washing the anion exchange resin;

d) drying the resin with flow of air or inert gas;
e) eluting [$^{18}$F]fluoride with a solution of a compound of formula (IV) in a $C_2$-$C_6$ alcohol;
f) evaporation of volatiles;
g) dissolution of the residue in a polar aprotic solvent;
h) heating of the resulting solution at 40-130° C. for 2-30 min;
i) addition of 85% $H_3PO_4$ or 10 M HCl to a solution of a resultant crude compound of formula [$^{18}$F]V;

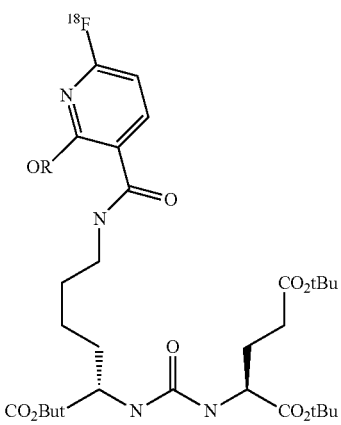

[18F]V wherein R is as defined for the compound of formula (IV),
j) heating of the resulting mixture at 40-130° C. for 2-30 min;
k) dilution of the reaction mixture and adjustment of the pH to 2.0-2.5 with an aqueous solution of a base;
l) RP HPLC purification by $H_3PO_4$ in aqueous EtOH as an eluent;
m) dilution with isotonic saline, adjustment of the pH with a base; and
n) sterile filtration.

11. A kit or a cassette system for preparing a compound of formula (I) according to claim 1, said kit or a cassette system comprises (i) an anion exchange column; (ii) a reaction vessel; (iii) vials containing aliquots eluents; (iv) a vial containing an aliquot of a compound of formula II or IV

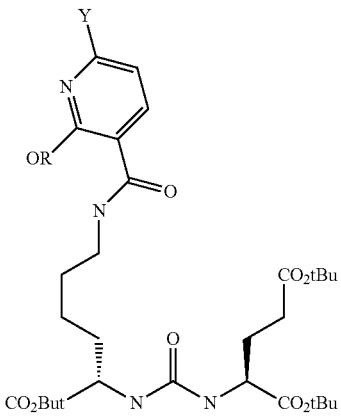

IV wherein
Y is $Me_3N^+Z^-$ or

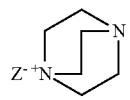

$Z^-$ is $CF_3SO_3$ or $CF_3CO_2$
R is $C_1$-$C_{10}$ substituted or unsubstituted alkyl, or C5-C12 unsubstituted or substituted aryl or heteroaryl;
(v) reagent vials wherein each reagent vial contains an aliquot of a reagent; (vi) optionally, one or more SPE columns for purification; (vii) optionally, a HPLC column for purification and, (viii) cleaning material for said reaction vessel and said SPE columns.

12. A pharmaceutical composition containing at least one compound of formula (I) according to claim 1 together with at least one pharmaceutically acceptable solvent, ingredient and/or diluent.

13. A method for imaging prostate cancer cells or prostate cancerous tissue, comprising administering to said prostate cancer cells or prostate cancerous tissue the pharmaceutical composition according to claim 12 and obtaining and image of said prostate cancer cells or prostate cancerous tissue.

14. A method of making a compound of formula (I) according to claim 1 from a compound of formula II and Lys-C(O)-Glu comprising:

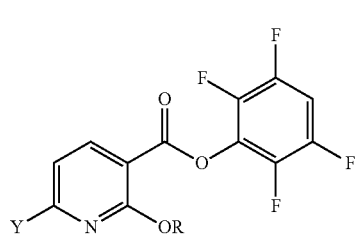

II

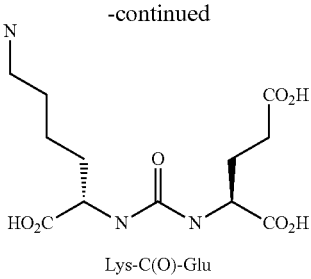

Lys-C(O)-Glu wherein
Y is Me$_3$N$^+$Z$^-$ or

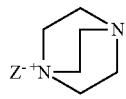

Z$^-$ is CF$_3$SO$_3$ or CF$_3$CO$_2$
R is C$_1$-C$_{10}$ substituted or unsubstituted alkyl, or C$_5$-C$_{12}$ unsubstituted or substituted aryl or heteroaryl,
a) providing an aqueous solution of [$^{18}$F]fluoride;
b) loading of [$^{18}$F]fluoride onto an anion exchange resin;
c) washing the anion exchange resin;
d) drying the resin with flow of air or inert gas;
e) elution of [$^{18}$F]fluoride with a solution of a compound of formula (II) in a polar aprotic solvent;
f) if the elution was carried out by a C$_2$-C$_6$ alcohol as solvent diluting the reaction mixture with a polar aprotic solvent;
g) heating of the resulting solution at 30-70° C. for 1-30 min which furnishes a crude of a compound of formula [$^{18}$F]III;

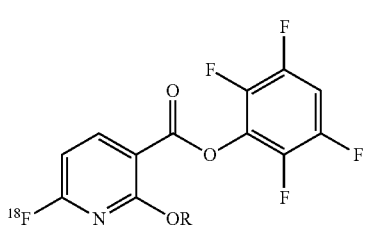

[18F]III wherein R is as defined for formula II,
h) purification of the compound of formula [$^{18}$F]III by reversed phase solid phase extraction (RP SPE) as follows: dilution of the resultant mixture with H$_2$O, loading the resulting solution on a RP SPE cartridge, washing the cartridge with H$_2$O, elution of the purified compound of formula [$^{18}$F]III with C$_2$-C$_6$ alcohol;
i) elution of the compound of formula [$^{18}$F]III directly to a solution of Lys-C(O)-Glu and a base in an anhydrous C$_2$-C$_6$ alcohol;
j) heating the resulting solution at 30-70° C. for 1-30 min;
k) purification of the resultant crude compound of formula I by RP SPE or alternatively RP HPLC; and
and wherein the method does not comprise an evaporation step; and/or a deprotection step; and/or a neutralization step.

15. A method of making a compound of formula (I) according to claim 1 from a compound of formula (IV) comprising:

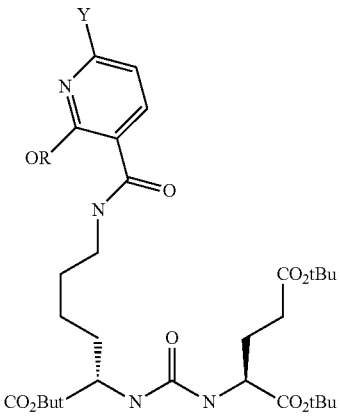

IV wherein
Y is Me$_3$N$^+$Z$^-$ or

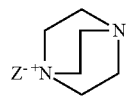

Z$^-$ is CF$_3$SO$_3$ or CF$_3$CO$_2$
R is C$_1$-C$_{10}$ substituted or unsubstituted alkyl, or C$_5$-C$_{12}$ unsubstituted or substituted aryl or heteroaryl,
a) providing an aqueous solution of [$^{18}$F]fluoride;
b) loading of [$^{18}$F]fluoride onto an anion exchange resin;
c) washing the anion exchange resin;
d) drying the resin with flow of air or inert gas;
e) eluting of [$^{18}$F]fluoride with a solution of a compound of formula (IV) in a C$_2$-C$_6$ alcohol;
g) dissolution of the residue in a polar aprotic solvent;
h) heating of the resulting solution at 40-130° C. for 2-30 min;
i) addition of 85% H$_3$PO$_4$ or 10 M HCl to a solution of a resultant crude compound of formula [$^{18}$F]V;

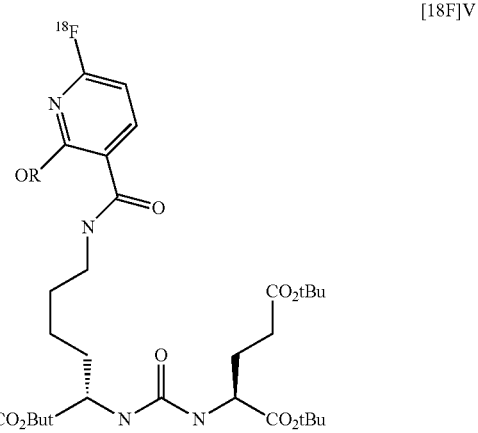

[18F]V wherein R is as defined for the compound of formula (IV),
j) heating of the resulting mixture at 40-130° C. for 2-30 min;
k) dilution of the reaction mixture and adjustment of the pH to 2.0-2.5 with an aqueous solution of a base;

l) RP HPLC purification by $H_3PO_4$ in aqueous EtOH as an eluent;

m) dilution with isotonic saline, adjustment of the pH with a base; and n) sterile filtration, and wherein the method does not comprise an evaporation step; and/or a deprotection step; and/or a neutralization step.

16. The compound of formula (I) according to claim 1 wherein R is allyl, propargyl, phenyl or pyridyl.

17. The method according to claim 9 of making a compound of formula (I) from a compound of formula II and Lys-C(O)-Glu comprising:

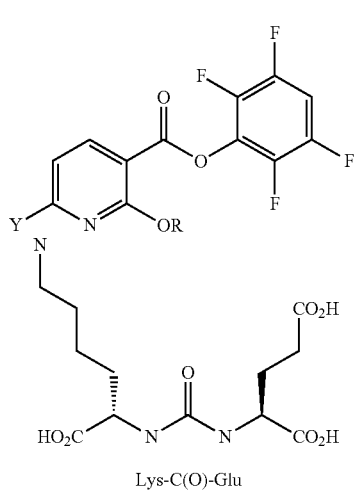

Lys-C(O)-Glu

Y is $Me_3N^+Z^-$ or

$Z^-$ is $CF_3SO_3$ or $CF_3CO_2$

R is methyl, ethyl, propyl, butyl, allyl, propargyl, phenyl or pyridyl, a) providing an aqueous solution of [$^{18}$F]fluoride;

b) loading of [$^{18}$F]fluoride onto an anion exchange resin;

c) washing the anion exchange resin;

d) drying the resin with flow of air or inert gas selected from the group consisting of He and Ar;

e) elution of [$^{18}$F]fluoride with a solution of a compound of formula (II) in a polar aprotic solvent selected from the group consisting of DMF, DMSO, MeCN and a $C_2$-$C_6$ alcohol or in a mixture thereof;

f) If the elution was carried out by a $C_2$-$C_6$ alcohol as the solvent, then diluting the reaction mixture with a polar aprotic solvent selected from the group consisting of DMF, DMSO, MeCN, and aprotic solvent/$C_2$-$C_6$ alcohol mixture;

g) heating the resulting solution at 40-50° C. for 2-7 min which furnishes a crude of a compound of formula [$^{18}$F]III;

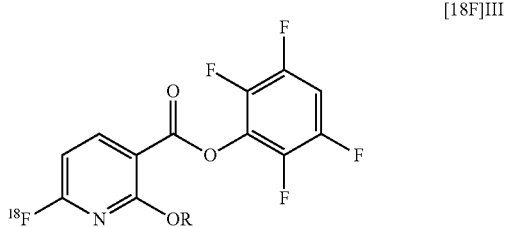

wherein R is as defined for formula II, h) purification of the compound of formula [$^{18}$F]III by reversed phase solid phase extraction (RP SPE) as follows: dilution of the above mixture with $H_2O$, loading the resulting solution on a RP SPE cartridge, washing the cartridge with $H_2O$, elution of the purified compound of formula [$^{18}$F]III with EtOH;

i) elution of the purified compound of formula [$^{18}$F]III directly to a solution of Lys-C(O)-Glu and a base selected from the group consisting of $CsHCO_3$, $RbHCO_3$, tetraalkylammonium phosphate, bicarbonate and carbonate in an anhydrous EtOH;

j) heating the resulting solution at 40-50° C. for 2-7 min;

k) purification of the resultant crude compound of formula I by RP SPE or alternatively RP HPLC; and l) optionally formulation.

18. The method according to claim 10 of making a compound of formula (I) from a compound of formula (IV) comprising:

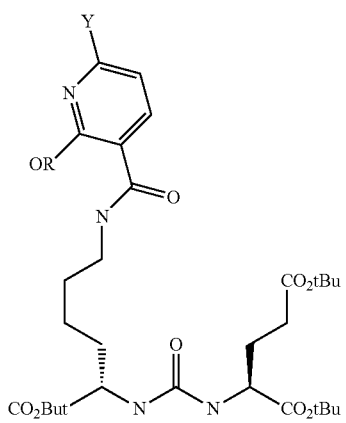

wherein

Y is $Me_3N^+Z^-$ or

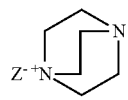

$Z^-$ is $CF_3SO_3$ or $CF_3CO_2$

R is methyl, ethyl, propyl, butyl, allyl, propargyl, phenyl or pyridyl, a) providing an aqueous solution of [$^{18}$F]fluoride;

b) loading of [$^{18}$F]fluoride onto an anion exchange resin;

c) washing the anion exchange resin;

d) drying the resin with flow of air or He or Ar;

e) eluting [$^{18}$F]fluoride with a solution of a compound of formula (IV) in MeOH;
f) evaporation of volatiles;
g) dissolution of the residue in a polar aprotic solvent selected from the group consisting of DMF, DMSO, and MeCN;
h) heating of the resulting solution at 40-130° C. for 2-30 min;
i) addition of 85% H$_3$PO$_4$ or 10 M HCl to a solution of a resultant crude compound of formula [$^{18}$F]V;

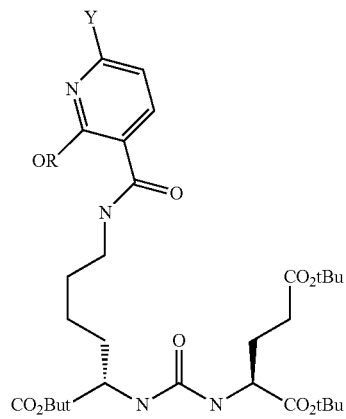

[18F]V wherein R is as defined for the compound of formula (IV),
j) heating of the resulting mixture at 40-130° C. for 2-30 min;
k) dilution of the reaction mixture and adjustment of the pH to 2.0-2.5 with an aqueous solution of a base selected from the group consisting of NaHCO$_3$, Na$_2$CO$_3$, Et$_3$N, NaOH, Na$_2$HPO$_4$ and Na$_3$PO$_4$;
l) RP HPLC purification by H$_3$PO$_4$ in aqueous EtOH as an eluent;
m) dilution with isotonic saline, adjustment of the pH with a base selected from the group consisting of NaHCO$_3$, Na$_2$CO$_3$, NaOH, Na$_2$HPO$_4$ and Na$_3$PO$_4$; and
n) sterile filtration.

19. The kit or a cassette system according to claim 11 for preparing a compound of formula (I), said kit or a cassette system comprises (i) an anion exchange column; (ii) a reaction vessel; (iii) vials containing aliquots eluents; (iv) a vial containing an aliquot of a compound of formula II or IV

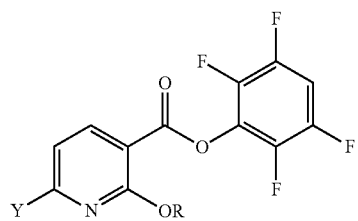

II

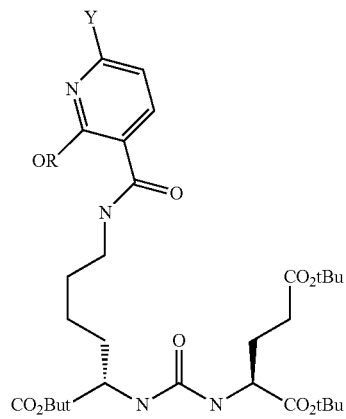

IV wherein
Y is Me$_3$N$^+$Z$^-$ or

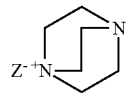

Z$^-$ is CF$_3$SO$_3$ or CF$_3$CO$_2$
R is methyl, ethyl, propyl, butyl, allyl, propargyl, phenyl or pyridyl;
(v) reagent vials wherein each reagent vial contains an aliquot of a reagent; (vi) optionally, one or more SPE columns for purification; (vii) optionally, a HPLC column for purification and, (viii) cleaning material for said reaction vessel and said SPE columns.

* * * * *